United States Patent

Klessig et al.

[11] Patent Number: 5,939,601
[45] Date of Patent: Aug. 17, 1999

[54] GENES ASSOCIATES WITH ENHANCED DISEASE RESISTANCE IN PLANTS

[75] Inventors: Daniel F. Klessig, Bridgewater; Yinong Yang, Piscataway, both of N.J.

[73] Assignee: Rutgers, The State University of New Jersey, New Brunswick, N.J.

[21] Appl. No.: 08/722,626

[22] Filed: Sep. 27, 1996

[51] Int. Cl.$^6$ .............................. C12N 15/29; A01H 5/10; A01H 4/00
[52] U.S. Cl. .................... 800/279; 800/279; 536/23.6; 435/172.3; 435/252.2; 435/320.1
[58] Field of Search .......................... 800/205, 250–255; 536/23.6; 435/172.3, 252.2, 320.1, 419, DIG. 43, DIG. 73

[56] References Cited

PUBLICATIONS

Broglie et al. Science. 1991. vol. 254: 1194–1197, 1991.
Avila et al. The Plant Journal. 1993. vol. 3: 553–563, 1993.
Dixon and Paiva. The Plant Cell. 1995. vol. 7: 1085–1097, 1995.
Urao et al. The Plant Cell. 1993. vol. 5: 1529–1539, 1993.
Uknes et al. the plant Cell. 1993. vol. 5: 159–169, 1993.
Malamy, J., et al. 1990 Science. 250, 1002–1004.
Metraux, J.P., et al. 1990 Science. 250, 1004–1006.
Gaffney, T., et al. 1993 Science. 261, 754–756.
Delaney T., et al. 1994 Science. 266, 1247–1250.
Klessig, D. F., et al. 1994 Plant Mol. Biol. 26, 1439–1458.
Chen, Z., et al., 1993 Science. 262, 1883–1886.
Durner, J., et al. 1995 Proc. Natl. Acad. Sci. USA 92, 11312–11316.
Dempsey, D.A., et al., 1995 Bull, Inst. Pasteur 93, 167–186.
Thompson, M.A. et al., 1995 BioEssay 17, 341–350.
Grotewold, E., et al., 1994 Cell 76, 543–53.
Solano, R., et al., 1995 EMBO J. 14, 1773.
Baranowskij, N., et al., 1994 EMBO J. 13, 5383.
Jackson, D., et al., 1991 Plant Cell 3, 115–125.
Sablowski, R.W., et al., 1994 EMBO J. 13, 128–137.
Oppenheimer, D.G., et al., 1991 Cell 67, 483–493.
Church, G.M., et al., 1984 Proc. Natl. Acad, Sci. USA 81, 1991–1995.
Malamy, J., et al., 1992 Plant Cell 4, 359–366.
Hennig, J., et al., 1993 Plant J. 4, 593–600.
Conrath, U., et al., 1995 Proc. Natl. Acad. Sci. USA 92, 7143–7147.
Payne, G., et al., 1988 Plant Mol. Biol. 11, 89–94.
Tice–Baldwin, K., et al., 1989 Science 246, 931–935.
Burk, O., et al., 1993 EMBO J. 12, 2027–2038.
Toth, C.R., et al., 1995 J. Biol. Chem. 270, 7661–7671.
Shreck, R., et al., 1991 EMBO. J. 10, 2247–2258.
Whitman, S., et al., 1994 Cell 78, 1101–1115.
Fang, K.S.F., et al., 1988 Proc. Natl. Acad. Sci. USA 85, 895–899.
Schuren, F.H.J., et al., 1993 J. Gen. Microbiol. 139, 2083–2090.
Murphy, E.V., et al., 1995 Gene 159, 131–135.
Alexander, D., et al., 1993 Proc. Natl. Acad. Sci. USA 90, 7327–7331.
Niderman, T., et al., 1995 Plant Physiol. 108, 17–27.
Mittler, R., et al., 1996 Trends in Microbiol. 4, 10–15.
An, G. 1986 Plant Physiol. 81: 86–91.
Gûbler, F. et al., 1995, Plant Cell 7, 1879–1891.
Gill, G., & Ptashne, M. 1988 Nature 334: 721–724.
Goff, S.A., et al., 1992 Genes Dev. 6: 864–875.
Horsche, R.G., et al., 1985 Science 227: 1229–1231.
Larkin, J.C., et al., 1994 Plant Cell 6: 1065–1076.
Topfer, R., et al., 1987 Nucl. Acids Res. 15: 5890.
Baulcombe, D.C., et al., 1996 Curr. Opin. Biotechnol. 7: 173–180.
R. Janknecht and T. Hunter 1996 Nature 383: 22–23.
C. Martin, 1996, Curr. Opin. Biotech 7: 130–138.

*Primary Examiner*—Douglas W. Robinson
*Assistant Examiner*—Ousama M-Faiz Zaghmout
*Attorney, Agent, or Firm*—Dann, Dorfman, Herrell and Skillman

[57] ABSTRACT

An isolated nucleic acid molecule is provided which encodes a tobacco myb homologue involved in the regulation of disease resistance in plants. The encoded protein comprises a basic N-terminal region with two imperfect tryptophan repeats of 53 and 51 amino acids, a potential ATP/GTP binding site or P-loop, a redox sensitive cysteine and a nuclear localization sequence. The acidic C terminus of Myb1 forms amphipathic α helices which are characteristic of transcriptional activation domains. The invention also provides novel Myb1 protein and antibodies thereto. Additionally, the invention provides novel transgenic plants with enhanced disease resistance to certain pathogens.

18 Claims, 9 Drawing Sheets

| | | | |
|---|---|---|---|
| 1 | MVRAPCCEKM | GLKKGPWIPE | EDQILISFIQ | TNGHGNWRAL |
| 41 | PKQAGLLRCG | KSCRLRWTNY | LRPDIKRGNF | TKEEEETIIQ |
| 81 | LHEMLGNRWS | AIAAKLPGRT | DNEIKNVWHT | HLKKKLKDYK |
| 121 | PPQNSKRHSK | SKNHDSKGPT | TSESSNNSDL | TIINTQKHID |
| 161 | SPVLAPNSPQ | ISSSTEMSTV | TLVDDHQMVV | IKQEVMESSE |
| 201 | YFPEIDESFW | TDELTTDNNW | SSTDHVMVAA | NQELQVQLPF |
| 241 | SSFKEENVDI | LATKMEDDMD | FWYNVFIKTD | DLPELPEF |

5,939,601

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 1344 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
      (A) NAME/KEY: Coding Sequence
      (B) LOCATION: 148...981
      (D) OTHER INFORMATION:

(xi) SEQUENCE DESCRIPTION: SEQ ID NO:1:

```
CTTTTTGGCA TTTCTTTCGT CCTTTTGGGA AGAAAGAAAG AGTGAAAGAA ATACCTAAAA      60

CCAAGGAGAA TTCAGAAAGA TAGCCGAAGA AGAAAAAAAA ACAAGTGATC AATTTTTCAA     120

GAGGAAGAAG AGATCAAGCA AAAGAAA ATG GTG AGA GCT CCT TGT TGT GAG AAA     174
                            Met Val Arg Ala Pro Cys Cys Glu Lys
                              1               5

ATG GGG CTG AAA AAA GGG CCA TGG ATT CCT GAA GAA GAT CAG ATT CTC      222
Met Gly Leu Lys Lys Gly Pro Trp Ile Pro Glu Glu Asp Gln Ile Leu
 10              15                  20                  25

ATC TCT TTC ATT CAA ACT AAT GGC CAT GGC AAC TGG CGA GCC CTT CCC      270
```

| | |
|---|---|
| Ile Ser Phe Ile Gln Thr Asn Gly His Gly Asn Trp Arg Ala Leu Pro<br>30 35 40 | |
| AAA CAG GCT GGA CTA TTG AGA TGC GGG AAG AGT TGC AGA CTG CGG TGG<br>Lys Gln Ala Gly Leu Leu Arg Cys Gly Lys Ser Cys Arg Leu Arg Trp<br>45 50 55 | 318 |
| ACG AAT TAT TTG CGA CCA GAT ATA AAG AGG GGA AAT TTC ACC AAG GAA<br>Thr Asn Tyr Leu Arg Pro Asp Ile Lys Arg Gly Asn Phe Thr Lys Glu<br>60 65 70 | 366 |
| GAA GAA GAA ACA ATT ATC CAG TTA CAT GAA ATG CTT GGC AAT AGA TGG<br>Glu Glu Glu Thr Ile Ile Gln Leu His Glu Met Leu Gly Asn Arg Trp<br>75 80 85 | 414 |
| TCT GCA ATA GCA GCA AAA TTA CCA GGA CGA ACA GAC AAT GAA ATA AAA<br>Ser Ala Ile Ala Ala Lys Leu Pro Gly Arg Thr Asp Asn Glu Ile Lys<br>90 95 100 105 | 462 |
| AAT GTT TGG CAC ACC CAC TTG AAG AAG AAG CTC AAA GAT TAT AAG CCT<br>Asn Val Trp His Thr His Leu Lys Lys Lys Leu Lys Asp Tyr Lys Pro<br>110 115 120 | 510 |
| CCT CAG AAC TCC AAA AGA CAC TCC AAG TCC AAG AAT CAT GAT TCC AAG<br>Pro Gln Asn Ser Lys Arg His Ser Lys Ser Lys Asn His Asp Ser Lys<br>125 130 135 | 558 |
| GGT CCT ACT ACT TCT GAA TCA TCC AAT AAT TCT GAT CTT ACT ATT ATT<br>Gly Pro Thr Thr Ser Glu Ser Ser Asn Asn Ser Asp Leu Thr Ile Ile<br>140 145 150 | 606 |
| AAT ACA CAA AAA CAC ATT GAT AGC CCA GTG CTA GCT CCT AAC TCA CCC<br>Asn Thr Gln Lys His Ile Asp Ser Pro Val Leu Ala Pro Asn Ser Pro<br>155 160 165 | 654 |
| CAA ATT TCA TCT AGT ACT GAA ATG TCA ACT GTG ACA CTA GTC GAT GAT<br>Gln Ile Ser Ser Ser Thr Glu Met Ser Thr Val Thr Leu Val Asp Asp<br>170 175 180 185 | 702 |
| CAT CAA ATG GTT GTG ATT AAG CAA GAA GTA ATG GAG TCG TCC GAG TAT<br>His Gln Met Val Val Ile Lys Gln Glu Val Met Glu Ser Ser Glu Tyr<br>190 195 200 | 750 |
| TTT CCA GAG ATC GAT GAG AGT TTT TGG ACG GAC GAA TTA ACA ACG GAC<br>Phe Pro Glu Ile Asp Glu Ser Phe Trp Thr Asp Glu Leu Thr Thr Asp<br>205 210 215 | 798 |
| AAT AAC TGG AGT AGT ACT GAT CAT GTT ATG GTT GCT GCT AAT CAA GAA<br>Asn Asn Trp Ser Ser Thr Asp His Val Met Val Ala Ala Asn Gln Glu<br>220 225 230 | 846 |
| TTA CAA GTT CAA TTA CCA TTT TCC AGT TTT AAG GAA GAA AAT GTG GAC<br>Leu Gln Val Gln Leu Pro Phe Ser Ser Phe Lys Glu Glu Asn Val Asp<br>235 240 245 | 894 |
| ATT TTG GCT ACA AAA ATG GAG GAT GAC ATG GAC TTT TGG TAC AAT GTT<br>Ile Leu Ala Thr Lys Met Glu Asp Asp Met Asp Phe Trp Tyr Asn Val<br>250 255 260 265 | 942 |
| TTC ATA AAG ACT GAT GAT TTG CCA GAA TTA CCA GAA TTT TGAGGGGGCT ATG<br>Phe Ile Lys Thr Asp Asp Leu Pro Glu Leu Pro Glu Phe<br>270 275 | 994 |
| TTATAATTTT GGTTCTTCTG TAAATTTTGA GGTAGTGGTA TCTAGCTAAT AAATAGGTTG | 1054 |
| TAGAGAATTT TTGGAGTCGG TAAGTTTGAA ACTTCGTGTT TGTAATTTTC TTGACCAGAA | 1114 |
| AAATTTCCCG TGTTGGGACC ATTAGCTAGT ATATTTTTGG TGTTAGTTAT TTTGAACCCT | 1174 |
| TCTTACTTAG TTTTAGTGGG AGAAGTGTAA GTGGATATGC TGATGTGTTT TGTATTGACT | 1234 |
| TAGGAATGTA GTTCCATATA TAGGCACAGA AAATCTATAT TTAGAGAAAA ATTATCGGAA | 1294 |
| AACCTATAGT CACCATCCTC CTAACTTAAC TTAAAAAAAA AAAAAAAAA | 1344 |

(2) INFORMATION FOR SEQ ID NO:2:

(i) SEQUENCE CHARACTERISTICS:
       (A) LENGTH: 278 amino acids (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:2:

Met Val Arg Ala Pro Cys Cys Glu Lys Met Gly Leu Lys Lys Gly Pro
 1               5                  10                  15

Trp Ile Pro Glu Glu Asp Gln Ile Leu Ile Ser Phe Ile Gln Thr Asn
                20                  25                  30

Gly His Gly Asn Trp Arg Ala Leu Pro Lys Gln Ala Gly Leu Leu Arg
            35                  40                  45

Cys Gly Lys Ser Cys Arg Leu Arg Trp Thr Asn Tyr Leu Arg Pro Asp
        50                  55                  60

Ile Lys Arg Gly Asn Phe Thr Lys Glu Glu Glu Thr Ile Ile Gln
 65                 70                  75                  80

Leu His Glu Met Leu Gly Asn Arg Trp Ser Ala Ile Ala Ala Lys Leu
                85                  90                  95

Pro Gly Arg Thr Asp Asn Glu Ile Lys Asn Val Trp His Thr His Leu
            100                 105                 110

Lys Lys Lys Leu Lys Asp Tyr Lys Pro Pro Gln Asn Ser Lys Arg His
        115                 120                 125

Ser Lys Ser Lys Asn His Asp Ser Lys Gly Pro Thr Thr Ser Glu Ser
130                 135                 140

Ser Asn Asn Ser Asp Leu Thr Ile Ile Asn Thr Gln Lys His Ile Asp
145                 150                 155                 160

Ser Pro Val Leu Ala Pro Asn Ser Pro Gln Ile Ser Ser Ser Thr Glu
                165                 170                 175

Met Ser Thr Val Thr Leu Val Asp Asp His Gln Met Val Val Ile Lys
            180                 185                 190

Gln Glu Val Met Glu Ser Ser Glu Tyr Phe Pro Glu Ile Asp Glu Ser
        195                 200                 205

Phe Trp Thr Asp Glu Leu Thr Thr Asp Asn Asn Trp Ser Ser Thr Asp
210                 215                 220

His Val Met Val Ala Ala Asn Gln Glu Leu Gln Val Gln Leu Pro Phe
225                 230                 235                 240

Ser Ser Phe Lys Glu Glu Asn Val Asp Ile Leu Ala Thr Lys Met Glu
                245                 250                 255

Asp Asp Met Asp Phe Trp Tyr Asn Val Phe Ile Lys Thr Asp Asp Leu
            260                 265                 270

Pro Glu Leu Pro Glu Phe
        275

(2) INFORMATION FOR SEQ ID NO:3:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:3:

CGGAATTCCC TAACTGACGC ATCGATGGGA                                     30

(2) INFORMATION FOR SEQ ID NO:4:

(i) SEQUENCE CHARACTERISTICS:
             (A) LENGTH: 30 bases
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

CGGAATTCCC TCCCTGACGC ATCGATGGGA                                     30

(2) INFORMATION FOR SEQ ID NO:5:

(i) SEQUENCE CHARACTERISTICS:
             (A) LENGTH: 30 bases
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

CGGAATTCTG TTTGGTATGC ATCGATGGGA                                     30

(2) INFORMATION FOR SEQ ID NO:6:

(i) SEQUENCE CHARACTERISTICS:
             (A) LENGTH: 30 bases
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

CGGAATTCTG TTGCCTATGC ATCGATGGGA                                                         30

(2) INFORMATION FOR SEQ ID NO:7:

(i) SEQUENCE CHARACTERISTICS:
            (A) LENGTH: 21 bases
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
            (A) NAME/KEY: Modified site
            (B) LOCATION: 6 ... 18
            (D) OTHER INFORMATION:
                N at the 6th position = A, C, G, or T
                N at the 9th position = C or T
                N at the 10th position = A or C
                N at the 12th position = A, C, G, or T
                N at the 13th position = C or T
                N at the 15th position = Inosine
                N at the 16th position = A or C
                N at the 18th position = Inosine (xi) SEQUENCE DESCRIPTION: SEQ ID NO:7:

AAGTCNTGNN GNNTNNGNTG G                                                                  21

(2) INFORMATION FOR SEQ ID NO:8:

(i) SEQUENCE CHARACTERISTICS:
            (A) LENGTH: 20 bases
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
            (A) NAME/KEY: Modified site
            (B) LOCATION: 3 ... 17
            (D) OTHER INFORMATION:
                N at the 3rd position = C or T
                N at the 12th position = A, C, G, or T
                N at the 15th position = A, C, G, or T
                N at the 17th position = G or T (xi) SEQUENCE DESCRIPTION: SEQ ID NO:8:

ATNTCGTTGT CNGTNCNNCC                                                                    20

(2) INFORMATION FOR SEQ ID NO:9:

(i) SEQUENCE CHARACTERISTICS:
            (A) LENGTH: 12 bases
            (B) TYPE: nucleic acid
            (C) STRANDEDNESS: single
            (D) TOPOLOGY: linear

```
    (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:9:

TCCCATCGAT GC                                                                12
```

GENES ASSOCIATES WITH ENHANCED DISEASE RESISTANCE IN PLANTS

Pursuant to 35 U.S.C. §202(c) it is acknowledged that the U.S. Government has certain rights in the invention described herein, which was made in part with funds from the National Science Foundation, Grant Number MCB-9320371.

FIELD OF THE INVENTION

This invention relates to the fields of molecular biology and genetic transformation in higher plants. More specifically, the invention provides novel plant genes and methods for altering expression levels of these genes to enhance a plant's resistance to certain pathogens.

BACKGROUND OF THE INVENTION

Several publications are referenced in this application by numerals in parenthesis in order to more fully describe the state of the art to which this invention pertains. Full citations for these references are found at the end of the specification. The disclosure of each of these publications is incorporated by reference herein.

Tobacco cultivars, such as *Nicotiana tabacum* Xanthi nc, which carry a dominant disease resistance gene (e.g., N gene) have been propagated. Infection of these plants with tobacco mosaic virus (TMV) results in a hypersensitive response. The hypersensitive response is characterized by host cell death and necrosis at the site of infection and restriction of pathogen growth and movement. Following induction of the hypersensitive response, systemic acquired resistance develops throughout the plant. Establishment of systemic acquired disease resistance results in enhanced resistance to a secondary challenge by the same and some unrelated pathogens.

An increasing body of evidence suggests that salicylic acid (SA) is an important component of the signal transduction pathway(s) leading to local and systemic plant defense responses, including the activation of pathogenesis-related (PR) proteins (1–5). Earlier studies suggest that one mechanism of SA action is to inhibit catalase and ascorbate peroxidase, thereby elevating endogenous $H_2O_2$ levels and generating salicylate free radicals (6–8; Chen and Klessig, unpublished data). The increased levels of $H_2O_2$ and/or products of reactions induced by salicylate free radicals such as lipid peroxide may act as signals for the activation of plant defense genes such as the PR-1 gene. However, little is known about the molecular mechanisms beyond these signals. Therefore, to facilitate the production of transgenic plants with enhanced resistance to certain pathogens, it is essential to identify other important genetic signaling components. The present invention relates to the identification and characterization of such components and provides methods for the generation of transgenic plants expressing these components. The transgenic plants so generated exhibit enhanced disease resistance to TMV and other plant pathogens.

SUMMARY OF THE INVENTION

This invention provides novel, biological molecules useful for identification, detection and/or regulation of complex signalling events that occur during the mounting of a disease resistance response in plants. According to one aspect of the present invention, an isolated nucleic acid is provided that includes an open reading frame encoding a Myb1 protein of a size about 278 amino acids in length. The protein comprises a basic N-terminal region with two imperfect tryptophan repeats of 53 and 51 amino acids, a potential ATP/GTP binding site or P-loop, a redox sensitive cysteine and a nuclear localization sequence. The acidic C terminus of Myb1 forms amphipathic α helices which are characteristic of transcriptional activation domains. In a preferred embodiment, an isolated nucleic acid is provided that includes an open reading frame encoding a tobacco Myb1 protein. In a particularly preferred embodiment, the Myb1 protein has the amino acid sequence of Sequence I.D. No. 2, (shown in FIG. 1A).

According to another aspect of the present invention, an isolated nucleic acid molecule is provided, which has a sequence selected from the group consisting of: 1) Sequence I.D. No. 1; 2) a sequence hybridizing with a unique coding region of the complementary strand of Sequence I.D. No. 1 and 3) a sequence encoding part or all of a polypeptide having amino acid sequence I.D. No. 2.

According to another aspect of the invention, an isolated Myb1 protein is provided which has a molecular weight of about 25 kD and 40 kD (preferably about 32 kD). The protein is of tobacco origin and has an amino acid sequence substantially the same as Sequence I.D. No. 2.

According to another aspect of the invention, antibodies immunologically specific for the proteins described hereinabove are provided.

Various terms relating to the biological molecules of the present invention are used hereinabove and also throughout the specifications and claims. The terms "substantially the same," "percent similarity" and "percent identity (identical)" are defined in detail in the description set forth below.

With reference to nucleic acids of the invention, the term "isolated nucleic acid" is sometimes used. This term, when applied to DNA, refers to a DNA molecule that is separated from sequences with which it is immediately contiguous (in the 5' and/or 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. Recombinant plasmids or vectors containing novel myb genes that may be propagated in *E. coli, S. cerevisiae* and Agrobacteria are contemplated for use in the present invention. These vectors may optionally contain strong constitutive promoter elements to facilitate high expression of the myb1 genes of the invention. Alternatively, they may contain inducible promoter elements so that expression of the myb1 genes of the invention can be controlled by addition of an inducer compound.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to antibodies of the invention, the term "immunologically specific" refers to antibodies that bind to one or more epitopes of a protein of interest (e.g., Myb1), but which do not immunospecifically recognize and bind other molecules in a sample containing a mixed population of antigenic biological molecules.

With respect to oligonucleotides, the term "specifically hybridizing" refers to the association between two single-stranded nucleotide molecules of sufficiently complementary sequence to permit such hybridization under predetermined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The nucleic acids, proteins and antibodies of the present invention are useful as research tools and will facilitate the elucidation of the mechanistic action of the novel genetic and protein interactions involved in the plant-microbe interactions. They should also find broad application in the generation of transgenic plants with enhanced disease resistance to certain pathogens.

DETAILED DESCRIPTION OF THE INVENTION

Figures 1A, 1B:
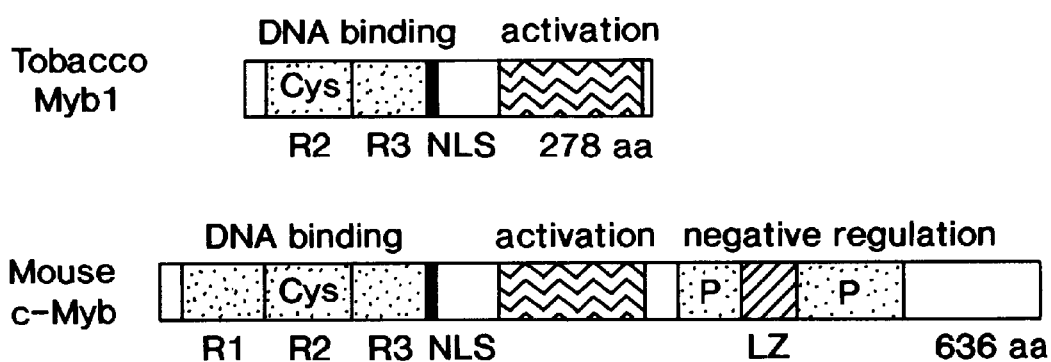
FIG. 1A shows the deduced amino acid sequence of the Myb1 protein (Sequence I.D. No. 2). The underlined sequences were used to design degenerate primers for the PCR amplification of the conserved regions of myb genes. The conserved redox sensitive cysteine residue at position 53 is indicated by a bold letter. The nucleotide sequence of myb1 (Sequence I.D. No. 1) has been submitted to GenBank (accession number not yet assigned).
FIG. 1B is a schematic comparison of structural features between Myb1 and the mouse c-Myb. R. tryptophan repeat; Cys, conserved redox sensitive cysteine (Cys-53 in Myb1 and Cys-130 in c-Myb); P, phosphorylation sites; NLS, nuclear localization sequences; LZ, leucine zipper; aa, amino acid residues.

Salicylic acid (SA) plays an important role in signaling the activation of plant defense responses against pathogen attack including, but not limited to, the induction of pathogenesis-related (PR) proteins. To gain further insight into the SA-mediated signal transduction pathway, a TMV-inducible myb oncogene homologue (myb1) from tobacco has been isolated and characterized. Induction of myb1 gene expression occurs upon TMV infection during both the hypersensitive response and during the development of systemic acquired resistance in resistant tobacco cultivar. Induction of myb1 occurs following the rise of endogenous salicylic acid. Myb1 induction was not observed in a susceptible cultivar which fails to accumulate SA. Expression of myb1 was also induced by incompatible bacterial pathogen *Pseudomonas syringae* pv. syringae during the hypersensitive response. Exogenous SA treatment rapidly (within 15 minutes) activated the expression of myb1 in both resistant and susceptible tobacco cultivars with the subsequent induction of PR genes occurring several hours later. Biologically active analogues of SA and 2,6-dichloroisonicotinic acid (INA, a synthetic functional analogue of SA), which induce PR genes and enhanced resistance, also activated the myb1 gene. In contrast, biologically inactive analogues were poor inducers of myb1 gene expression. Furthermore, the recombinant Myb1 protein was shown to specifically bind to a Myb-binding consensus sequence found in the promoter of the PR-1a gene. Transgenic tobacco plants carrying sense or anti-sense myb1 constructs did not show constitutive expression of PR-1 genes, but did exhibit enhanced resistance to TMV and *Rhizoctonia solani*. Taken together, these results suggest that the tobacco myb1 gene encodes a signaling component downstream of SA which participates in plant disease resistance.

Oncogenes such as myb play an important role in animal pathogenesis and the immune response; by analogy, their plant homologues also appear to function in plant pathogenesis and defense responses. Animal myb genes encode transcription factors involved in cell cycling, proliferation and differentiation. The c-myb gene, the cellular counterpart of the transforming gene (v-myb) of the avian myeloblastosis virus, is essential for the development of hematopoietic tissue, including the formation of lymphocytes and other leukocytes important for the immune response. The Myb protein not only regulates the expression of cell proliferation genes (e.g., c-myc, DNA-polymerase-α and p34cdc2), but also activates genes related to the immune response and pathogenesis (e.g., lysozyme, mim-1, CD4, and T-cell receptors) (9, 10).

During the past several years plant homologues of myb oncogenes have been isolated from maize, barley, petunia, potato, Antirrhinum and Arabidopsis (11–19). They were shown to regulate flavonoid biosynthesis in maize (11) and Antirrhinum (16) and to determine epidermal cell (trichome) differentiation in Arabidopsis (17). Recently, myb genes have also been shown to be involved in dehydration and salt stress of Arabidopsis (18) and the gibberellin-response pathway of barley (19). However, their involvement in plant-microbe interactions has not yet been demonstrated. Methods for the isolation and characterization of a tobacco myb oncogene homologue that is induced by TMV infection are provided herein. The encoded tobacco protein, designated Myb1, appears to function as a signaling component downstream of SA where it participates in transcriptional regulation of plant defense responses.

I. Preparation of Myb1-Encoding Nucleic Acid Molecules, Myb1 Proteins, and Antibodies Thereto A. Nucleic Acid Molecules Nucleic acid molecules encoding the Myb1 proteins of the invention may be prepared by two general methods: (1) They may be synthesized from appropriate nucleotide triphosphates, or (2) they may be isolated from biological sources. Both methods utilize protocols well known in the art.

The availability of nucleotide sequence information, such as the full length cDNA having Sequence I.D. No. 1, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 1.3 kb double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 1.3 kb double-stranded molecule. A synthetic DNA molecule so constructed may then be cloned and amplified in an appropriate vector.

Nucleic acid sequences encoding Myb1 may be isolated from appropriate biological sources using methods known in the art. In a preferred embodiment, a cDNA clone is isolated from an expression library of tobacco origin. In an alternative embodiment, genomic clones encoding Myb1 may be isolated. Alternatively, CDNA or genomic clones encoding from other plant or animal species may be obtained.

In accordance with the present invention, nucleic acids having the appropriate level of sequence homology with the protein coding region of Sequence I.D. No. 1 may be identified by using hybridization and washing conditions of appropriate stringency. For example, hybridizations may be performed, according to the method of Sambrook et al., (22) using a hybridization solution comprising: 5× SSC, 5× Denhardt's reagent, 1.0% SDS, 100 μg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2× SSC and 1% SDS; (2) 15 minutes at room temperature in 2× SSC and 0.1% SDS; (3) 30 minutes-1 hour at 37° C. in 1× SSC and 1% SDS; (4) 2 hours at 42–65° in 1× SSC and 1% SDS, changing the solution every 30 minutes.

Nucleic acids of the present invention may be maintained as DNA in any convenient cloning vector. In a preferred embodiment, clones are maintained in plasmid cloning/ expression vector, such as pbluescript (Stratagene, La Jolla, Calif.), which is propagated in a suitable *E. coli* host cell.

Myb1-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having Sequence I.D. No. 1. Such oligonucleotides are useful as probes for detecting or isolating myb1 genes in other plant species.

B. Proteins

A full-length Myb1 protein of the present invention may be prepared in a variety of ways, according to known methods. The protein may be purified from appropriate sources, e.g., plant or animal cultured cells or tissues, by immunoaffinity purification. However, this is not a preferred method due to the low amount of protein likely to be present in a given cell type at any time.

The availability of nucleic acids molecules encoding Myb1 enables production of the protein using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

Alternatively, according to a preferred embodiment, larger quantities of Myb1 may be produced by expression in a suitable procaryotic or eucaryotic system. For example, part or all of a DNA molecule, such as the cDNA having Sequence I.D. No. 1, may be inserted into a plasmid vector adapted for expression in a bacterial cell, such as *E. coli*, or into a baculovirus vector for expression in an insect cell. Such vectors comprise the regulatory elements necessary for expression of the DNA in the host cell (e.g. *E. coli* or insect cell), positioned in such a manner as to permit expression of the DNA in the host cell. Such regulatory elements required for expression include promoter sequences, transcription initiation sequences and, optionally, enhancer sequences.

The Myb1 produced by gene expression in a recombinant procaryotic or eucyarotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6–8 histidine residues at their N-terminus or C-terminus. Such methods are commonly used by skilled practitioners.

The Myb1 proteins of the invention, prepared by the aforementioned methods, may be analyzed according to standard procedures. For example, such proteins may be subjected to amino acid sequence analysis, according to known methods.

The present invention also provides antibodies capable of immunospecifically binding to proteins of the invention. Polyclonal antibodies directed toward Myb1 may be prepared according to standard methods. In a preferred embodiment, monoclonal antibodies are prepared, which react immunospecifically with various epitopes of Myb1. Monoclonal antibodies may be prepared according to general methods of Köhler and Milstein, following standard protocols. Polyclonal or monoclonal antibodies that immunospecifically interact with Myb1 can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-Myb1 antibodies are described below.

II. Uses of Myb1-Encoding Nucleic Acids, Myb1 Proteins and Antibodies Thereto

The potential of recombinant genetic engineering methods to enhance disease resistance in agronomically important plants has received considerable attention in recent years. Protocols are currently available for the stable introduction and/or augmentation of expression of genes in plants. The present invention provides nucleic acid sequences which, upon stable introduction into a recipient plant, enhance a plant's ability to survive pathogen attack. Myb1 proteins of the invention may also be used as a research tool to identify other proteins that are intimately involved in both the hypersensitive and acquired disease resistance responses in plants.

A. Myb1-Encoding Nucleic Acids

Myb1-encoding nucleic acids may be used for a variety of purposes in accordance with the present invention. Myb1-encoding DNA, RNA, or fragments thereof may be used as probes to detect the presence of and/or expression of genes encoding Myb1 protein. Methods in which Myb1-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

The Myb1-encoding nucleic acids of the invention may also be utilized as probes to identify related genes from other plant species. As is well known in the art, hybridization stringencies may be adjusted to allow hybridization of nucleic acid probes with complementary sequences of varying degrees of homology. Thus, Myb1-encoding nucleic acids may be used to advantage to identify and characterize other genes of varying degrees of relation to myb1, thereby enabling further characterization of the signalling cascade involved in the control of disease resistance in plants. Additionally, they may be used to identify genes encoding proteins that interact with Myb1 (e.g., by the "interaction trap" technique), which should further accelerate elucidation of these cellular signalling mechanisms.

Nucleic acid molecules, or fragments thereof, encoding Myb1 may also be utilized to control the production of Myb1, thereby regulating the amount of protein available to participate in disease resistance signalling pathways. Alterations in the physiological amount of Myb1 protein may act synergistically with other agents used to protect plants during pathogen attack. In one embodiment, the nucleic acid molecules of the invention may be used to decrease expression of myb1. In this embodiment, full-length antisense molecules are employed which are targeted to myb1-encoding genes. The use of antisense molecules to decrease expression levels of a predetermined gene is known in the art.

In another embodiment, overexpression of the myb1 gene is induced in a target population of plant cells to generate a co-suppression effect. This excess expression serves to promote downregulation of both endogenous and exogenous myb1 genes. In other cases, overexpression can lead to overproduction of the encoded protein, Myb1. Overproduction of Myb1 in transgenic plant cells may be assessed by immunofluorescence or any other standard technique known in the art. Alternatively, overexpression of Myb1 by this method may facilitate the isolation and characterization of other components involved in the protein-protein complex formation that occurs during the initiation of the disease resistance response pathway in plants.

As described above, Myb1-encoding nucleic acids are also used to advantage to produce large quantities of substantially pure Myb1 protein, or selected portions thereof.

B. Myb1 Protein and Antibodies

Purified Myb1, or fragments thereof, may be used to produce polyclonal or monoclonal antibodies which also may serve as sensitive detection reagents for the presence and accumulation of Myb1 (or complexes containing Myb1) in plants or in cultured plant cells. Recombinant techniques enable expression of fusion proteins containing part or all of the Myb1 protein. The full length protein or fragments of the protein may be used to advantage to generate an array of monoclonal antibodies specific for various epitopes of the protein, thereby providing even greater sensitivity for detection of the protein in plants and their cells.

Polyclonal or monoclonal antibodies immunologically specific for Myb1 may be used in a variety of assays designed to detect and quantitate the protein. Such assays include, but are not limited to: (1) flow cytometric analysis; (2) immunochemical localization of Myb1 in plant cells; and (3) immunoblot analysis (e.g., dot blot, Western blot) of extracts from various plant cells. Additionally, as described above, anti-Myb1 can be used for purification of Myb1 (e.g., affinity column purification, immunoprecipitation).

From the foregoing discussion, it can be seen that Myb1-encoding nucleic acids, myb1 expressing vectors, Myb1 proteins and anti-Myb1 antibodies of the invention can be used to detect myb1 gene expression and alter Myb1 protein accumulation for purposes of assessing the genetic and protein interactions involved in the regulation of the disease resistance pathway in plants and for enhancing disease resistance in plants.

MATERIALS AND METHODS

A. Chemicals and Plant Materials.

SA and its analogues were purchased from Sigma or Aldrich. The *Nicotiana tabacum* cvs. Xanthi nc (NN genotype) and Xanthi (nn genotype), *N. sylvestris*, and *N. tomentosiformis* were grown in growth rooms at 22° C. in a 14-hour light cycle for 6 to 8 weeks before being used in experimentation.

B. Pathogen Inoculations and Chemical Treatments.

Two leaves on each tobacco plant were inoculated with TMV strain U1 at a concentration of 1 μg/ml in 50 mM phosphate buffer (pH 7.0) by rubbing with carborundum. Mock-inoculated plants were rubbed with buffer and carborundum. In temperature-shift experiments, plants were moved to 32° C. after TMV inoculation and incubated for 48 hours before shifting to 22° C. For bacterial infection, suspensions of *Pseudomonas syringae* pv. syringae strain Pss61 was adjusted in 5 mM $MgSO_4$ solution to $2 \times 10^8$ cells/ml and infiltrated into tobacco leaves. For chemical treatments, tobacco leaves were pricked with a needle and then infiltrated with 1 mM solutions of SA, INA or their analogues (adjusted to pH 6.5 with KOH). In cycloheximide tests, leaves were pretreated with CHX (0.3 mM) for 30 minutes as described (20) before injection of SA (1 mM) plus CHX (0.3 mM). All experiments were performed at least twice.

C. Isolation and Sequencing of the myb1 cDNA.

Two degenerate oligonucleotides corresponding to highly conserved regions of Myb proteins were synthesized: Sequence I.D. No. 7: forward, 5'-AAGTCNTG(C/T) (A/C) GN(C/T)TI (A/C) GITGG-3'; sequence I.D. No. 8: reverse, 5'-AT(C/T)TCGTTGTCNGTNC(G/T) NCC-3'. DNA purified from a tobacco cDNA library (made from TMV-infected leaf mRNA, Guo and Klessig, unpublished data) was used as the template for PCR reactions. The amplified PCR fragments were purified on a 2.5% agarose gel and cloned into pGEM-T vector (Promega). After one of the PCR fragments was identified to be part of a TMV-inducible myb gene by RNA blot analysis, it was used as a probe to screen approximately $10^6$ plaques of the TMV-induced tobacco cDNA library. Positive plaques were purified by a second round of plaque hybridization. The pBK-CMV phagemid containing the myb1 cDNA was excised in vivo from the ZAP Express vector using the ExAssist helper phage (Stratagene). The sequence of myb1 was determined for both strands by the dideoxy sequencing method and analyzed using the LASERGENE software (DNASTAR, Inc.) and GCG package (ver. 7.0, University of Wisconsin).

D. DNA and RNA Analysis.

DNA and RNA were purified from leaf tissues by phenol/chloroform extraction. Fifteen micrograms of genomic DNA was digested with restriction enzymes, fractionated on a 1% agarose gel and blotted onto a nylon membrane (Nytran Plus, Schleicher & Shuell). For detection of myb1 mRNA, 25 μg of total RNA was fractionated on a 1.5% agarose gel containing formaldehyde and blotted onto a nylon membrane. The [$\alpha$-$^{32}$P]-dCTP-labeled probe corresponding to the gene specific 3' region (from 724 to 1344 bp of myb1) was made by the random-priming method with an oligolabeling kit (Pharmacia). Hybridization and washing were performed according to the method of Church and Gilbert (21).

E. Production and Purification of the Recombinant Myb1 Protein.

The myb1 cDNA was recloned into the NdeI/Xho site of the pET28a(+) vector (Novagen) and the in-frame fusion was verified by DNA sequencing. Cells of *Escherichia coli* strain BL21 (DE3) transformed with the recombinant plasmid were grown at 37° C. in LB medium (22) containing 50 μg/ml kanamycin. The production of the polyhistidine-Myb1 fusion protein was induced in mid-logarithmic *E. coli* cultures by addition of isopropyl β-D-thiogalactopyranoside (IPTG, 1 mM). After 3 hours of growth at 30° C., bacterial cells were harvested and proteins were purified on nickel chelate affinity columns as described by the manufacturer (Novagen). The purified Myb1 protein was eluted from the column using the elution buffer (20 mM Tris, pH 7.9, 500 mM NaCl and 500 mM imidazole) and stored at −80° C. after addition of glycerol to 20%. Protein concentrations were determined with a Bradford reagent (Bio-Rad).

F. Gel Mobility Shift Assay.

The PR-1a promoter fragments were amplified by PCR and labeled by filling the 5' overhangs with [α-$^{32}$P]-dATP and the Klenow fragment. MBSI (5'-CGGAATTCCCTAACTGACGCATCGATGGGA-3') and MBSII (5'-CGGAATTCTGTTTGGTATGCATCGATGGGA-3') oligonucleotides and their mutated forms (FIG. 8B) were annealed with a primer, Sequence I.D. No. 9: 5'-TCCCATCGATGC-3', and then extended with the Klenow fragment in presence of [α-$^{32}$P]-dCTP to make double-stranded probes for the assay. DNA binding reactions were performed in 20 µl of binding buffer (10 mM Tris, pH 8.0, 50 mM Nadl, 1 mM dithiothreitol, 1 mM EDTA, 1 mg/ml BSA and 10% glycerol) that contained 2 µg of double-stranded poly(dI-dC), 200 ng of the purified recombinant Myb1 protein and 0.5–2 ng of $^{32}$P-labeled probe (10,000–40,000 cpm). After incubation at 4° C. for 30 minutes, the reaction mixtures were electrophoresed on a 5% polyacrylamide gel in 0.5× Tris-borate-EDTA buffer (22) at 100 V. The gels were then dried and autoradiographed.

G. Plasmid Construction and Tobacco Transformation.

Tobacco myb1 cDNA was fused to cauliflower mosaic virus (CaMV) 35S promoter in both sense and antisense orientations. For the sense construct, myb1 cDNA was cleaved with EcoRI and end-blunted with Klenow, followed by XbaI digestion. The 1.3 kb fragment containing the myb1 cDNA was cloned into pRT103 (45) after digestion with MscI and XbaI. The resulting chimeric gene contains myb1 fused to the CaMV 35S promoter and polyadenylation signal in a sense orientation.

Two types of antisense constructs were generated. One antisense construct contained myb1 with its 5' untranslated region. This was obtained by cleavage of a XhoI fragment containing myb1 from the sense construct described above. The resulting mixture of vector and myb1-containing XhoI fragments was religated and plasmids were screened to identify those in which myb1 was fused to CaMV 35S promoter in an antisense orientation. The other antisense construct contained a myb1 sequence that lacked the 5' untranslated region and first 8 bp of the coding sequence. This was obtained by cloning the SacI/XhoI fragment of the myb1 cDNA into pRT103, which had been digested with SacI and XhoI. All chimeric genes were subsequently cloned into the HindIII site of the binary vector pGA482 (39). Transgenic tobacco (*N. tabacum* cv. Xanthi nc) plants were generated using the Agrobacterium-mediated leaf disk transformation procedure (43).

H. Analysis of Disease Resistance to TMV.

To analyze TMV-resistance level, 8 week old transgenic tobacco plants were inoculated with TMV at a concentration of 1 µg/ml in 50 mM phosphate buffer (pH 7.0). Lesion size was measured 6–7 days after inoculation. In addition, lesion development was closely monitored for several transgenic plants by measuring lesion size during the course of viral infection (2 to 6 days after inoculation). The development of viral lesions was also documented by photography.

TMV accumulation during the course of infection was determined by assaying the amount of viral coat protein in infected tobacco leaves. For each time point, three lesions were punched out using a cork borer (0.7 cm in diameter). Leaf discs were homogenized in extraction buffer (50 mM Tris, pH 8.0, 1 mM EDTA, 12 mM β-mercaptoethanol, 0.5 mM phenylmethylsufonyl fluoride). After clarification by centrifugation, 15 µl of the extracts were fractionated by SDS-PAGE. The amount of coat protein was determined by immunoblot analysis with a rabbit polyclonal antibody, which specifically recognizes the TMV coat protein.

I. Infection Assays with *Rhizoctonia solani*.

The fungus *Rhizoctonia solani* was propagated on solid potato-dextrose medium (PDA, Difco) at 25° C. Fungal mycelial suspension was made by mixing the dried mycelia with water in a household blender at medium speed for 10 minutes. The fungal suspension was then thoroughly mixed with soil in a proportion such that all of the vector-only transformed control seedlings showed severe disease symptoms. Tobacco seedlings (18 days old) were transplanted into inoculated soil and grown at 22° C. in a growth chamber with a 16 hour light cycle. The disease symptoms of seedlings were monitored every 2 days from 4–20 days post infection.

The definitions set forth below are provided to facilitate understanding of the subject matter of the present invention:

Pathogen-inoculated refers to the inoculation of a plant with an avirulent pathogen on a resistant host plant.

The term promoter region refers to the 5' regulatory regions of a gene. In the present invention, the use of both strong constitutive gene promoters and inducible gene promoters is contemplated.

The term operably linked means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The term DNA construct refers to genetic sequence used to transform plants and generate progeny transgenic plants. These constructs may be administered to plants in a viral or plasmid vector. Other methods of delivery such as electroporation, Polyethylene glycol mediated transformation, vacuum infiltration, Agrobacterium T-DNA mediated transformation and transformation using the biolistic process are also contemplated to be within the scope of the present invention. Standard methods for delivery of DNA and protocols for preparing the transforming DNA may be found in *Current Protocols in Molecular Biology*, eds. Frederick M. Ausubel et al., John Wiley & Sons, 1995.

The following specific examples are provided to illustrate embodiments of the invention. They are not intended to limit the scope of the invention in any way.

EXAMPLE I

I.A Cloning and Sequence Analysis of a TMV-inducible myb Homologue.

To assess the role of myb homologues in the interaction between tobacco and TMV, PCR fragments (160 bp) of tobacco myb genes were amplified and cloned from TMV-induced tobacco cDNAs using degenerate oligonucleotide primers corresponding to highly conserved regions of Myb proteins (underlined in FIG. 1A). Twenty myb PCR fragments were subjected to sequence analysis. Three groups of myb fragments were isolated with significant (56%–72%) DNA sequence identity. Based on northern analysis, one group was found to be induced upon TMV infection. The corresponding TMV-inducible tobacco myb gene, designated myb1, was isolated by screening a cDNA library made from the resistant tobacco cultivar Xanthi nc after TMV infection. This cDNA is 1344 bp in length and contains a 194 bp 5' untranslated region and a 363 bp 3' untranslated region with a typical polyadenylation signal. The open reading frame encodes a full length Myb1 protein of 278 amino acid residues with a predicted molecular mass of 32 kD (FIG. 1A). The hydrophilic Myb1 protein has a calculated isoelectric point of 5.62. Among Myb proteins, the basic N-terminal region is conserved. In the tobacco Myb1, it is composed of two imperfect tryptophan repeats of 53 (residue 12 to 64) and 51 (residue 65 to 115) amino acids, while the mouse c-Myb contains three tryptophan repeats (R1-R3, FIG. 1B). Secondary structure analyses of Myb1 (and mouse c-Myb) predict that the tryptophan repeats form helix-turn-helix DNA-binding motifs. Myb1 and c-Myb also share a potential ATP/GTP-binding site (P-loop), a redox sensitive cysteine, and a nuclear localization sequence within their N-terminal DNA-binding domains. The acidic C-terminal region of Myb1 (residue 179 to 278, pI 3.6) forms amphipathic α-helices, which are characteristic of transcriptional activation domains. The corresponding activation domain of the mouse c-Myb does not share sequence homology with Myb1 and is bounded on its C-terminal ends by a large phosphorylatible negative regulatory domain which controls the activity of c-Myb (FIG. 1B). This negative regulatory domain is absent from Myb1. The DNA sequence of myb1 (Sequence I.D. No. 1) is set forth below:

```
   1 CTTTTTGGCA TTTCTTTCGT CCTTTTGGGA AGAAAGAAAG AGTGAAAGAA
  51 ATACCTAAAA CCAAGGAGAA TTCAGAAAGA TAGCCGAAGA AGAAAAAAAA
 101 ACAAGTGATC AATTTTTCAA GAGGAAGAAG AGATCAAGCA AAAGAAAATG
 151 GTGAGAGCTC CTTGTTGTGA GAAAATGGGG CTGAAAAAAG GGCCATGGAT
 201 TCCTGAAGAA GATCAGATTC TCATCTCTTT CATTCAAACT AATGGCCATG
 251 GCAACTGGCG AGCCCTTCCC AAACAGGCTG GACTATTGAG ATGCGGGAAG
 301 AGTTGCAGAC TGCGGTGGAC GAATTATTTG CGACCAGATA TAAAGAGGGG
 351 AAATTTCACC AAGGAAGAAG AAGAAACAAT TATCCAGTTA CATGAAATGC
 401 TTGGCAATAG ATGGTCTGCA ATAGCAGCAA AATTACCAGG ACGAACAGAC
 451 AATGAAATAA AAAATGTTTG GCACACCCAC TTGAAGAAGA AGCTCAAAGA
 501 TTATAAGCCT CCTCAGAACT CCAAAAGACA CTCCAAGTCC AAGAATCATG
 551 ATTCCAAGGG TCCTACTACT TCTGAATCAT CCAATAATTC TGATCTTACT
 601 ATTATTAATA CACAAAAACA CATTGATAGC CCAGTGCTAG CTCCTAACTC
 651 ACCCCAAATT TCATCTAGTA CTGAAATGTC AACTGTGACA CTAGTCGATG
 701 ATCATCAAAT GGTTGTGATT AAGCAAGAAG TAATGGAGTC GTCCGAGTAT
 751 TTTCCAGAGA TCGATGAGAG TTTTTGGACG GACGAATTAA CAACGGACAA
 801 TAACTGGAGT AGTACTGATC ATGTTATGGT TGCTGCTAAT CAAGAATTAC
 851 AAGTTCAATT ACCATTTTCC AGTTTTAAGG AAGAAAATGT GGACATTTTG
 901 GCTACAAAAA TGGAGGATGA CATGGACTTT TGGTACAATG TTTTCATAAA
 951 GACTGATGAT TTGCCAGAAT TACCAGAATT TTGAGGGGGC TATGTTATAA
1001 TTTTGGTTCT TCTGTAAATT TTGAGGTAGT GGTATCTAGC TAATAAATAG
1051 GTTGTAGAGA ATTTTTGGAG TCGGTAAGTT TGAAACTTCG TGTTTGTAAT
1101 TTTCTTGACC AGAAAAATTT CCCGTGTTGG GACCATTAGC TAGTATATTT
1151 TTGGTGTTAG TTATTTTGAA CCCTTCTTAC TTAGTTTTAG TGGGAGAAGT
1201 GTAAGTGGAT ATGCTGATGT GTTTTGTATT GACTTAGGAA TGTAGTTCCA
1251 TATATAGGCA CAGAAAATCT ATATTTAGAG AAAAATTATC GGAAAACCTA
1301 TAGTCACCAT CCTCCTAACT TAACTTAAAA AAAAAAAAA AAAA
```

The putative DNA-binding domain of the tobacco Myb1 is highly homologous with that of animal and plant Myb proteins. Amino acid sequence comparisons of the DNA-binding domains reveal that Myb1 is 90% identical to Myb.Ph2 of petunia (12), 52% identical to Atmyb2 of Arabidopsis(18) and 45% identical to mouse c-Myb (9). Outside of the DNA-binding domain, only petunia Myb.Ph2 shows limited homology with the C-terminal region of Myb1. In contrast to tobacco Myb1, Myb.Ph2 is constitutively expressed in petunia leaf tissues (12).

Figure 2:
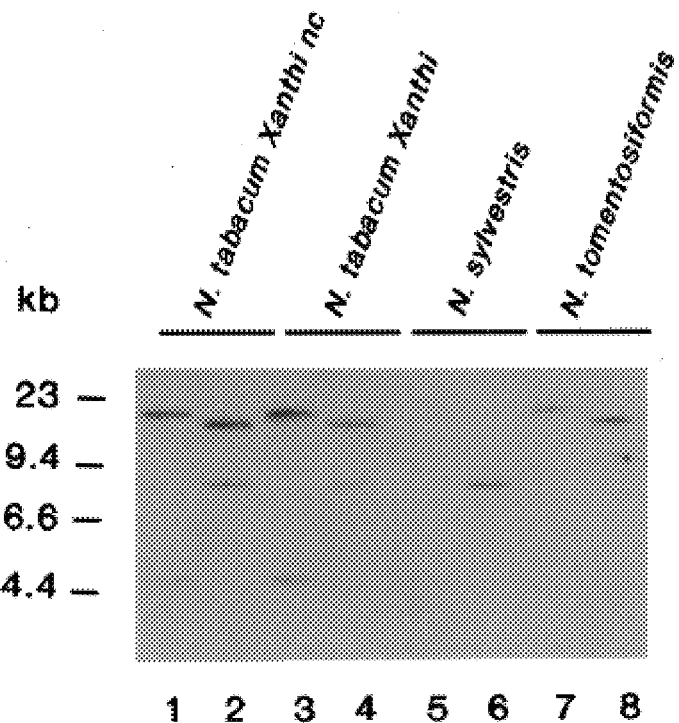
FIG. 2 is an autoradiogram showing the results of Southern analysis of the myb1 gene using genomic DNAs from several Nicotiana species. The genomic DNAs (15 μg.) of the amphidiploid N. tabacum (cvs. Xanthi nc and Xanthi) and its parental diploid species, N. sylvestris and N. tomentosiformis were digested with EcoRI (lane 1, 3, 5, 7) or HindIII (lane 2, 4, 6, 8). After blotting, the DNAs were hybridized with a gene-specific myb1 probe.

Southern analysis of tobacco (cvs. Xanthi nc and Xanthi) genomic DNAs digested with EcoRI and HindIII identified two bands when probed with the gene-specific 3' region (from position 724 bp to 1344 bp) of myb1 cDNA (FIG. 2). The two copies of myb1 found in the amphidiploid N. tabacum cultivars are probably derived from the diploid parental species N. sylvestris and N. tomentosiforxmis as one of the two bands was present in N. sylvestris and the other in N. tomentosiformis. Two different size RNAs (1.4 kb and 1.2 kb) which hybridized with the gene-specific myb1 probe were found in *N. tabacum* (see FIG. 3). Since both RNAs were also detected in *N. sylvestris* and *N. tomentosiformis* which contain only one myb1 gene each, they are likely the result of alternative splicing of the myb1 transcript.

IB. Induction of myb1 Expression by TMV and Bacterial Infections.

Figure 3A:
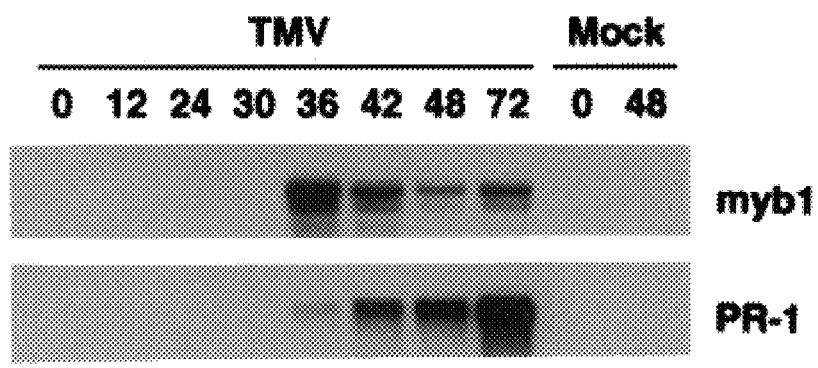
FIG. 3A depicts RNA blot analysis of myb1 and PR-1 gene expression following TMV infection at 22° C. in the resistant tobacco cultivar Xanthi nc. Time is indicated in hours post infection.

The expression of myb1 in response to TMV infection was examined. RNA blots were prepared from mock- and TMV-infected tobacco and were probed with the 3' gene-specific myb1 cDNA. The blots were also probed with a cDNA for the PR-1 genes. PR-1 genes serve as a molecular markers for activation of plant defense responses. The myb1 genes were not detected in healthy tobacco leaves, but were induced to low levels by 30 hours and to high levels by 36 hours after TMV infection at 22° C. in Xanthi nc, which carries the N resistance gene (FIG. 3A). The kinetics of myb1 expression closely paralleled the rise of endogenous SA levels which occurs between 24 to 36 hours after TMV inoculation (1). Expression of myb1 peaked at 36 hours after infection, preceding activation of the PR-1 genes whose MRNA continued to rise through at least 72 hours post inoculation. In contrast, activation of myb1 was not observed in the TMV-infected susceptible cultivar Xanthi which lacks the N gene and does not accumulate SA or express PR genes (1). Additionally, activation of the myb1 gene did not occur in response to wounding with a hemostat or by rubbing with carborundum (i.e., mock inoculation in FIG. 3).

Figure 3B:
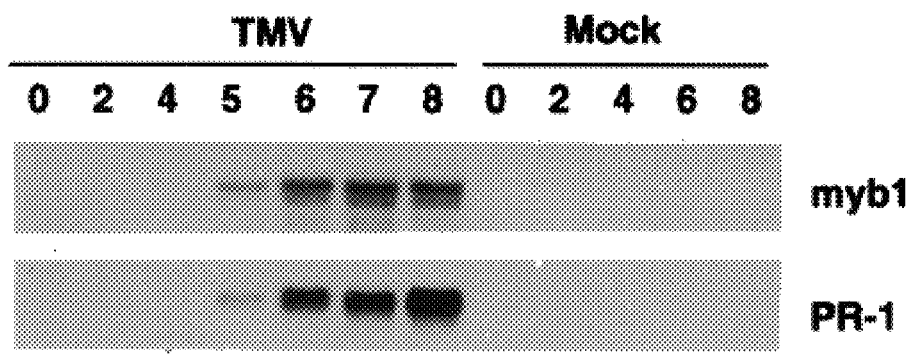
FIG. 3B is also an RNA blot illustrating accumulation of myb1 and PR-1 mRNA following shift of Xanthi nc plants from a temperature where resistance to TMV can not develop (32° C.) to a temperature at which resistance is established (22° C.). RNAs were isolated from inoculated leaves. Time is indicated in hours post temperature shift. TMV- and mock-inoculated plants were maintained at 32° C. for 48 hours after inoculation before being exposed to 22° C. temperatures.

In cultivars containing the N gene, resistance to TMV is reversibly blocked at high temperatures (>28° C.) and elevation of SA levels and PR-1 gene activation is not observed. Shifting infected plants to a lower temperature (e.g., 22° C.) results in i) a rapid and dramatic rise in SA between 4 to 6 hours, ii) activation of PR-1 genes and iii) development of resistance (23). At the high temperature (32° C.), TMV-infected Xanthi nc also failed to express myb1 genes while transfer to a lower temperature (22° C.) resulted in activation of myb1 and PR-1 within 5 hours (FIG. 3B).

Figure 4:
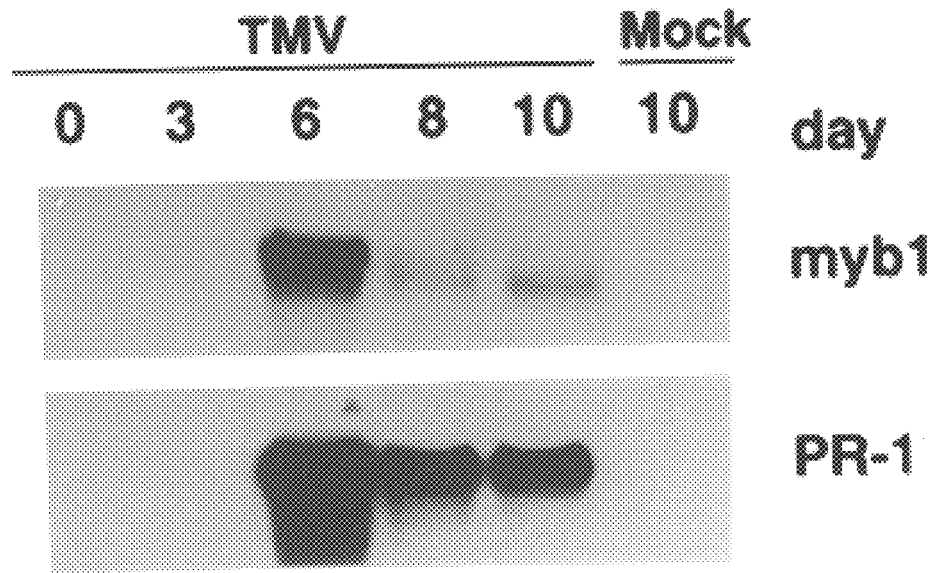
FIG. 4 is an RNA blot illustrating induction of myb1 by TMV infections during development of systemic acquired resistance. RNA was isolated from upper, uninoculated leaves of the resistant tobacco cultivar Xanthi nc following TMV infection of lower leaves. Time is indicated in days post infection.

Systemic expression of myb1 was also analyzed in TMV infected tobacco (FIG. 4). Expression of the myb1 gene, as well as PR-1 genes, was induced in upper, uninoculated leaves within 6 days after TMV inoculation of lower leaves. Therefore, activation of myb1 is associated with both the hypersensitive response in local, infected leaves, and also with the development of systemic acquired resistance in distal, uninfected leaves.

Figure 5:
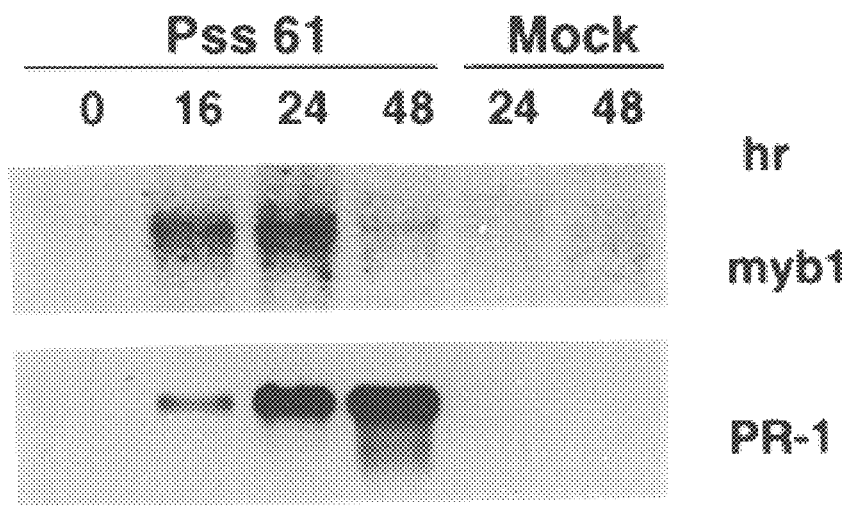
FIG. 5 is an RNA blot illustrating induction of myb1 by an incompatible bacterial pathogen. RNA was isolated from tobacco leaves infected with *Pseudomonas syringae* pv. syringae strain Pss61 or mock-inoculated with 5 mM $MgSO_4$ solution. Time is indicated in hours post infection.

To provide further evidence for the importance of myb1 expression in plant-pathogen interactions, the bacterial pathogen *Pseudomonas syringae* pv. syringae strain Pss61 was tested for its ability to induce myb1 expression. Pss61 is an incompatible pathogen of tobacco and elicits a rapid hypersensitive response. Infection of tobacco with Pss61 induced myb1 expression within 16 hours, closely followed by the continuous accumulation of PR-1 mRNAs (FIG. 5).

IC. Rapid Activation of myb1 Expression by SA, INA, and Their Biologically Active Analogues.

Since the induction of myb1 appears to follow the rise of endogenous SA levels in TMV-infected tobacco leaves, SA treatments were tested for activation of expression of myb1. Exogenous application of 1 mM SA induced expression of myb1 within 15 minutes in both the resistant cultivar Xanthi nc (FIG. 6A) and the susceptible cultivar Xanthi. Activation of myb1 by SA was transient, with myb1 mRNA levels peaking at 30 minutes and then rapidly declining. This may be due to rapid inactivation of SA via glycosylation in tobacco leaves (24). In contrast, PR-1 induction did not occur until between 6 to 12 hours after treatment.

Figure 6A:
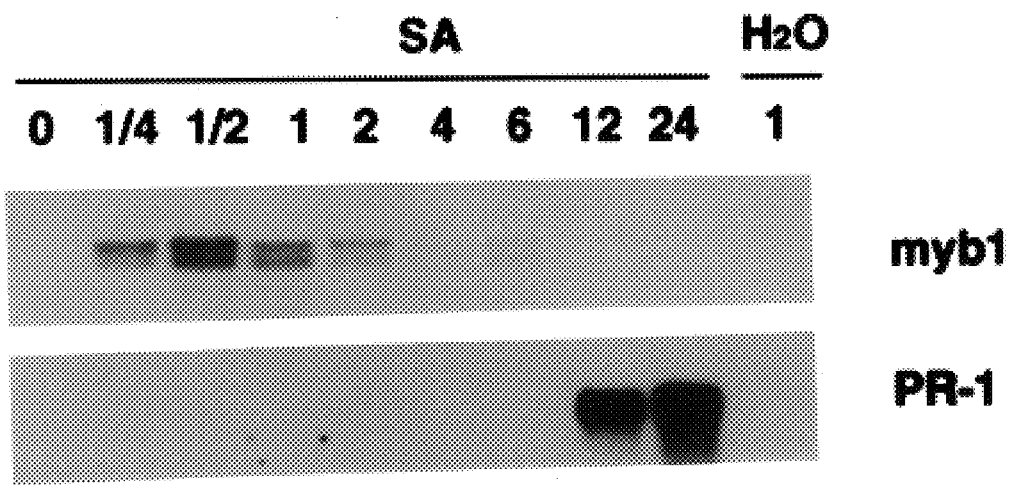
FIG. 6A is an RNA blot depicting the effect of salicylic acid (SA) on myb1 gene expression. Activation of myb1 by SA (1 mM) preceded induction of PR-1. Time is indicated in hours post injection of SA (or $H_2O$ as a control) into tobacco leaves.
Figure 6B:
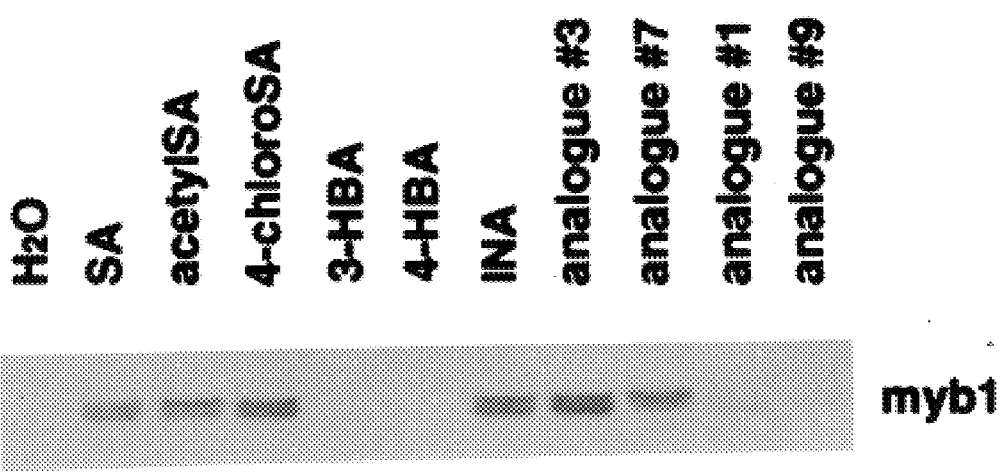
FIG. 6B is an RNA blot illustrating induction of myb1 by SA, 2,6-dichloroisonicotinic acid (INA) and their analogues biologically active analogues (acetylSA, 4-chloroSA, analogues #3 and #7). Inactive analogues (3- and 4-hydroxybenzoic acid, analogues #1 and #9) were poor inducers. Expression of myb1 was analyzed 30 minutes after injection with 1 mM of the various compounds. The chemical structures of the INA analogues were presented in a previous report (25).

The synthetic compound 2,6-dichloroisonicotinic acid (INA) is a potent inducer of PR genes and enhanced disease resistance and appears to act as a functional analogue of SA (7, 25). INA also induced myb1 expression (FIG. 6B). To further assess the functional relevance of SA and INA in the activation of myb1, several analogues of SA and INA were compared for their ability to activate myb1 expression. Expression of myb1 was effectively activated by the biologically active analogues of both SA and INA (acetylSA and 4-chloroSA) (analogues #3 and #7). Biologically inactive analogues (3-hydroxybenzoic acid, 4-hydroxybenzoic acid, analogues #1 and #9) were not as effective in activating myb1 expression (FIG. 6B). Thus, there is a good correlation between the biological activity of SA and INA analogues and the ability to induce myb1 gene expression.

ID. Effect of Cycloheximide on myb1 Expression.

Figure 7:
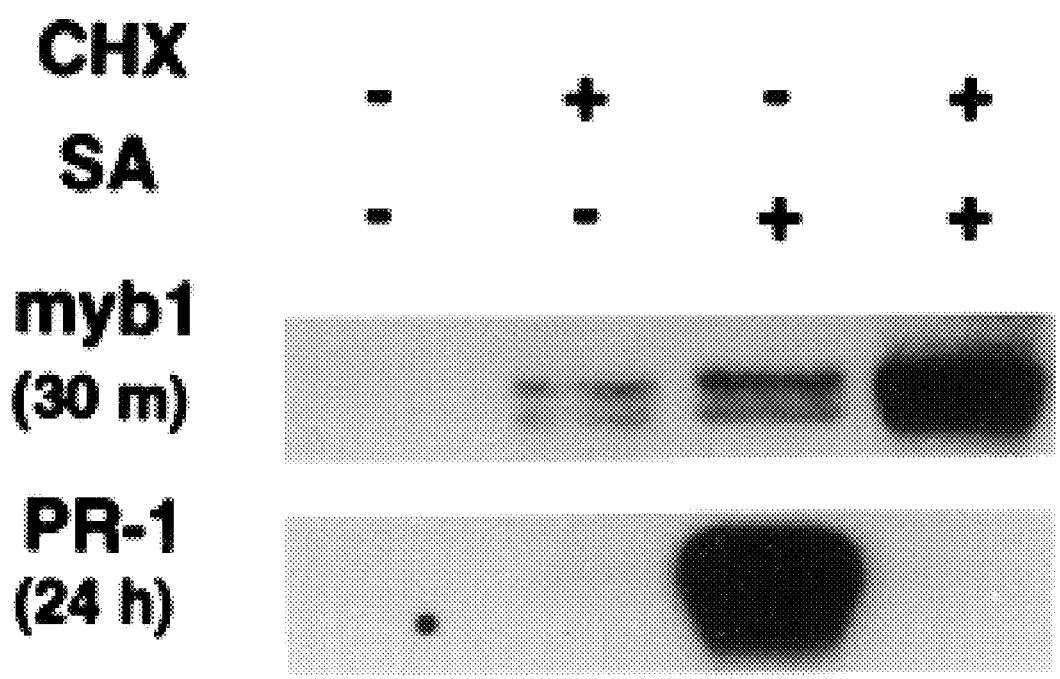
FIG. 7 shows RNA blot analysis of tobacco leaves pretreated with cycloheximide (CHX) (0.3 mM) for 30 minutes followed by treatment with SA (1 mM) plus CHX (0.3 mM) for an additional 30 minutes or 24 hours.

The rapid activation of myb1 by SA suggested that this induction did not require synthesis of a new protein(s). To test this possibility, protein synthesis was blocked by pretreatment for 30 minutes with cycloheximide (CHX) before addition of SA and CHX. As anticipated, CHX did not inhibit SA-mediated activation of myb1 (FIG. 7). However, CHX treatment alone induced the myb1 genes and greatly enhanced their expression when combined with SA. This is similar to barley GAmyb expression in response to CHX and gibberellin treatments (19). In contrast, SA induction of PR-1 genes was blocked by CHX, in agreement with a previous report (20).

IE. Myb1 Binds Specifically to the PR-1a Promoter.

Induction of PR-1 genes by SA required de novo protein synthesis as demonstrated above. The tobacco Myb1 protein may be one of these newly synthesized factors since activation of myb1 by SA preceded the expression of PR-1 genes (FIG. 6). In fact, sequence analysis uncovered multiple Myb-binding sites (MBS) in the promoters of several PR genes including PR-1 and PR-2 (encoding β-1,3-glucanase). Myb proteins are known to bind to two types of MBS. Type I (MBSI) has the consensus sequence (T/C)AAC(T/G)G and is bound by animal and some plant Myb proteins (10, 18). Type II (MBSII) has the consensus sequence G(G/T)T(A/T)G (G/T)T and is bound by several plant Myb proteins (11, 13, 16). The PR-1a promoter (26) contains both types of binding sites: MBSI (TAACTG) located at −169 to −174 and MBSII (GTTTGGT) at −520 to −514. In addition, four MBSI-like sites, with five of six nucleotides matching the consensus sequence, are positioned at −643 to −639 (AACTG), −526 to −522 (AACTG), −332 to −328 (TAACG), and −241 to −237 (TAACT).

Figures 8A, 8B:
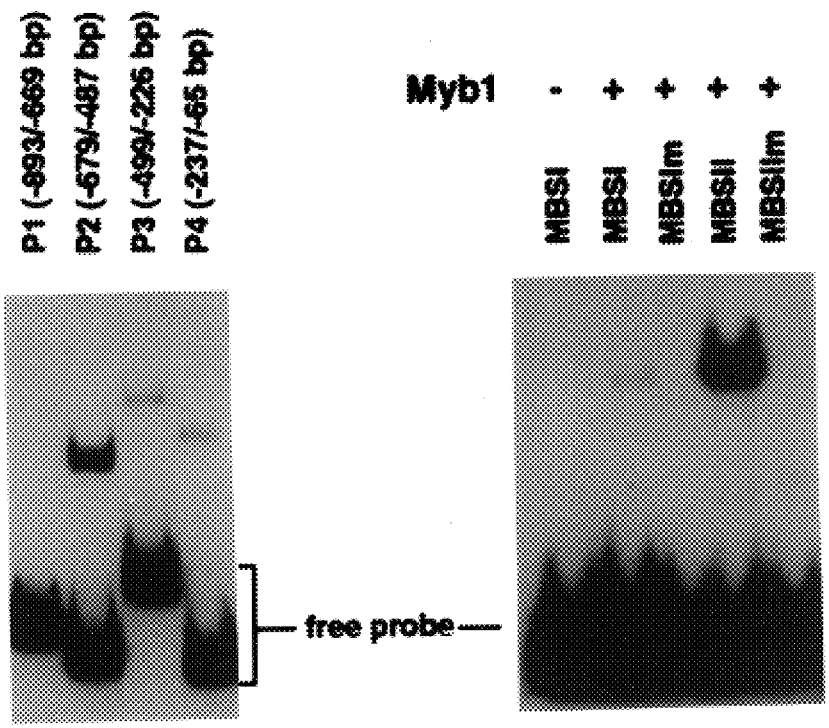
FIG. 8A shows the results of gel mobility shift assays with purified recombinant Myb1 protein and DNA-binding activity of Myb1 to several PR-1a promoter fragments. The locations of the fragments in the PR-1a promoter relative to the transcriptional start site are given in parenthesis.
FIG. 8B shows the results of a gel mobility shift assay illustrating the preferential binding of Myb1 protein to MBSII (GTTTGGT) found in PR-1a promoter fragment P2. The binding reaction fractionated in the first lane did not contain Myb1 while those in other lanes contained 200 ng of Myb1. The following double-strand oligonucleotides were used as probes: MBSI, Sequence I.D. No. 3: 5'-CGGAATTCCCTAACTGACGCATCGATGGGA-3'; MBSIm, Sequence I.D. No. 4: 5'-CGGAATTCCCTCCCTGA CGCATCGATGGGA-3'; MBSII, Sequence I.D. No. 5: 5'-CGGAATTCTGTTTGGTATGCATCGATGGGA-3'; and MBSIIm, Sequence I.D. No. 6: 5'-CGGAATTCTGTTGCCTAT GCATCGATGGGA-3'.

To examine the interaction between the Myb1 protein and the PR-1a promoter, the histidine-tagged recombinant Myb1 protein was produced in *E. coli* and purified by nickel affinity chromatography. Using the gel mobility shift assay, purified Myb1 was found to strongly bind to the P2 fragment (−679 to −487) of the PR-1a promoter which contains a MBSII (GTTTGGT) and two MBSI-like sites. (FIG. 8A). Myb1 also weakly bound to the P4 fragment (−237 to −65) which contains a MBSI (TAACTG) and to the P3 fragment (−499 to −226) which contains two type I-like sites. Myb1 did not bind to the P1 fragment (−893 to −669) which does not contain MBS.

To prove that Myb1 indeed binds to MBS in the PR-1a promoter, 30 bp oligonucleotides containing MBSI (TAACTG), MBSII (GTTTGGT) or their mutated forms were synthesized, labeled and used in the gel mobility shift assay. Myb1 preferentially bound to MBSII and only very weakly bound to MBSI (FIG. 8B). It did not bind the mutated forms of MBSI and MBSII. Therefore, the tobacco Myb1 protein indeed binds to MBS in the PR-1a promoter. The much higher binding affinity for MBSII is in agreement with its stronger binding of the P2 fragment (which contains MBSII) than the P4 fragment (which contains MBSI).

Figure 8C:
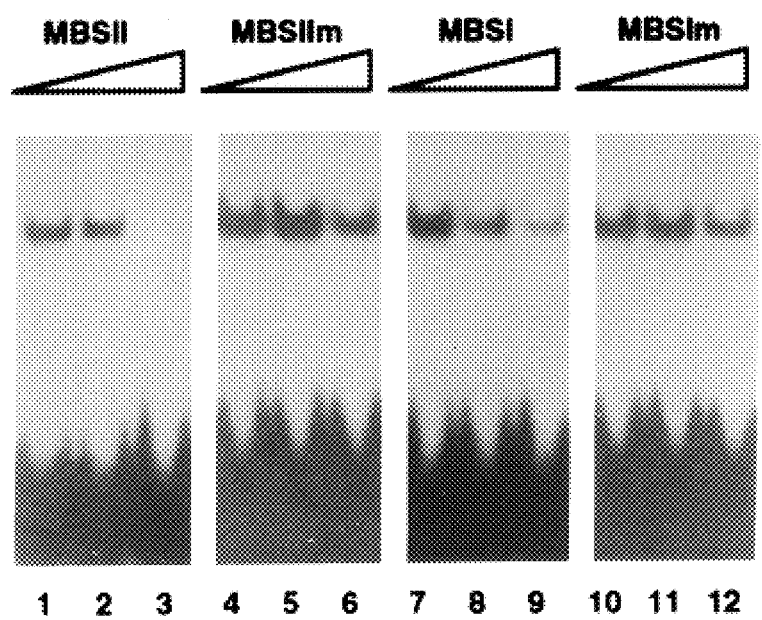
FIG. 8C is a gel showing the competition for binding of Myb1 to the MBSII probe. The binding assay was performed by preincubating unlabeled competitor oligonucleotides for 15 minutes with Myb1 before addition of 1 ng of $^{32}P$ labeled MBSII probe. Reactions fractionated in lanes 1, 4, 7, and 10 contained no competitors, while those in lanes 2, 5, 8, and 11 contained 20 ng competitors and those in lanes 3, 6, 9, and 12 contained 200 ng competitors.

To further demonstrate the specific binding of Myb1 to MBSII, competition experiments were performed with MBSII as the labeled probe. Binding of Myb1 to MBSII was effectively reduced by the addition of unlabeled MBSII (FIG. 8C). In contrast, competition by MBSI was less effective, while the mutated forms of MBSI and MBSII had marginal effects on binding. In summary, Myb1 preferentially bound to MBSII in the PR-1a promoter, suggesting that Myb1 may be involved in the transcriptional activation of this gene during plant defense responses.

EXAMPLE II

Construction and Analysis of myb1 Transgenic Plants.

The myb1 gene was placed in a sense or antisense orientation under the control of the constitutive and powerful CaMV 35S promoter and introduced into the tobacco cultivar Xanthi nc. Ninety independent transgenic tobacco plants were generated. Sixteen vector-only transformed plants were also generated to be used as controls. Analysis of transgenic plants containing the sense construct (pGAY1.6 and pGAY1.8) indicated that overexpression of the myb1 transgene did not lead to the constitutive expression of PR-1 genes. Nonetheless, almost half of the sense myb1 transgenic plants exhibited enhanced resistance towards TMV infection as indicated by up to 40% reduction in viral lesion size (Table I). Surprisingly, an even greater percentage (58%) of transgenic plants carrying antisense constructs (pGAY8.2 and PGAY 5.4) showed enhanced resistance. These results are analyzed further in the Discussion section.

TABLE I

Resistance of T1 Generation of myb1 Transgenic Plants to TMV

| Construct[a] | # Transgenic lines | # Resistant plants[b] | % of Resistant Plants |
|---|---|---|---|
| pGA482 | 16 | 0 | 0 |
| pGAY1.6 & 1.8 | 49 | 22 | 45 |
| pGAY8.2 | 25 | 12 | 48 |
| pGAY5.4 | 16 | 12 | 75 |

[a]pGA482 is a binary vector containing no insert. pGAY1.6 & 1.8 contain 35S:myb1 in a sense orientation. pGAY8.2 contains, in antisense orientation, myb1 with its 5' untranslated region. pGAY5.4 contains antisense myb1 without its 5' untranslated region and first 8 bp of the coding sequence.
[b]Resistance was determined based on reduced lesion size.

To examine whether the enhanced resistance is an inheritable trait, seeds of the primary transgenic plants (T1 generation) were collected and progeny from several lines were further analyzed for their resistance to TMV. The results summarized in Table II are from the progeny of six representative lines that exhibited enhanced resistance to TMV in the T1 generation. At least 5 out of the 6 lines produced progeny that maintained the disease resistance trait, as shown by reduced lesion size. The level of resistance to TMV in T2 generation was similar to that of T1 generation, with up to approximately 40% reduction in lesion size. Again, resistance to TMV appears to be more consistently elevated in transgenic plants containing the antisense constructs.

TABLE II

Resistance of T2 Generation of myb1 Transgenic Plants to TMV

| Line[a] | | Lesion Diameter (mm)[b] | Reduction in lesion size (%) |
|---|---|---|---|
| 482-1 | (1,2,6,8) | 2.84 ± 0.17 | |
| 482-12 | (1,3,4,8) | 3.19 ± 0.30 | |
| 1.6-1 | (1) | 2.07 ± 0.31 | 31 |
| | (2) | 2.71 ± 0.40 | 11 |
| | (7) | 1.90 ± 0.27 | 37 |
| | (8) | 2.00 ± 0.27 | 34 |
| 1.8-8 | (2) | 1.96 ± 0.25 | 35 |
| | (3) | 2.50 ± 0.32 | 17 |
| | (4) | 2.78 ± 0.39 | 5 |
| | (8) | 2.85 ± 0.43 | 6 |
| 8.2-10 | (3) | 1.77 ± 0.23 | 41 |
| | (4) | 1.79 ± 0.32 | 41 |
| | (5) | 1.79 ± 0.26 | 41 |
| | (6) | 1.80 ± 0.27 | 40 |
| 8.2-11 | (2) | 1.96 ± 0.30 | 35 |
| | (4) | 2.04 ± 0.25 | 32 |
| | (7) | 1.95 ± 0.31 | 35 |
| | (8) | 1.83 ± 0.28 | 39 |
| 5.4-1 | (1) | 2.12 ± 0.44 | 30 |
| | (2) | 1.83 ± 0.37 | 39 |
| | (5) | 1.89 ± 0.32 | 37 |
| | (6) | 2.31 ± 0.41 | 24 |
| 5.4-12 | (1) | 2.81 ± 0.38 | 7 |
| | (2) | 3.11 ± 0.44 | 0 |
| | (4) | 2.59 ± 0.48 | 14 |
| | (7) | 2.60 ± 0.43 | 14 |

[a]Lines 482-1 and 482-12 are vector-only transformed control plants. Lines 1.6-1 and 1.8-8 are transgenic plants containing the 35S:myb1 construct in a sense orientation. Lines 8.2-10 and 8.2-11 are transgenic plants containing a myb1 antisense construct with its 5' untranslated region. Lines 5.4-1 and 5.4-12 are transgenic plants containing an antisense construct without the 5' untranslated region and first 8 base pairsof the coding sequence. The numbers in parenthesis designate individual plants from the indicated lines.
[b]Lesion diameter was measured at 6 days post inoculation. Data show the mean diameter and standard deviation for 20 lesions measured per plant, except in the case of lines 482-1 and 482-12, in which measurements of 80 lesions from 4 plants were averaged.

Figure 9:
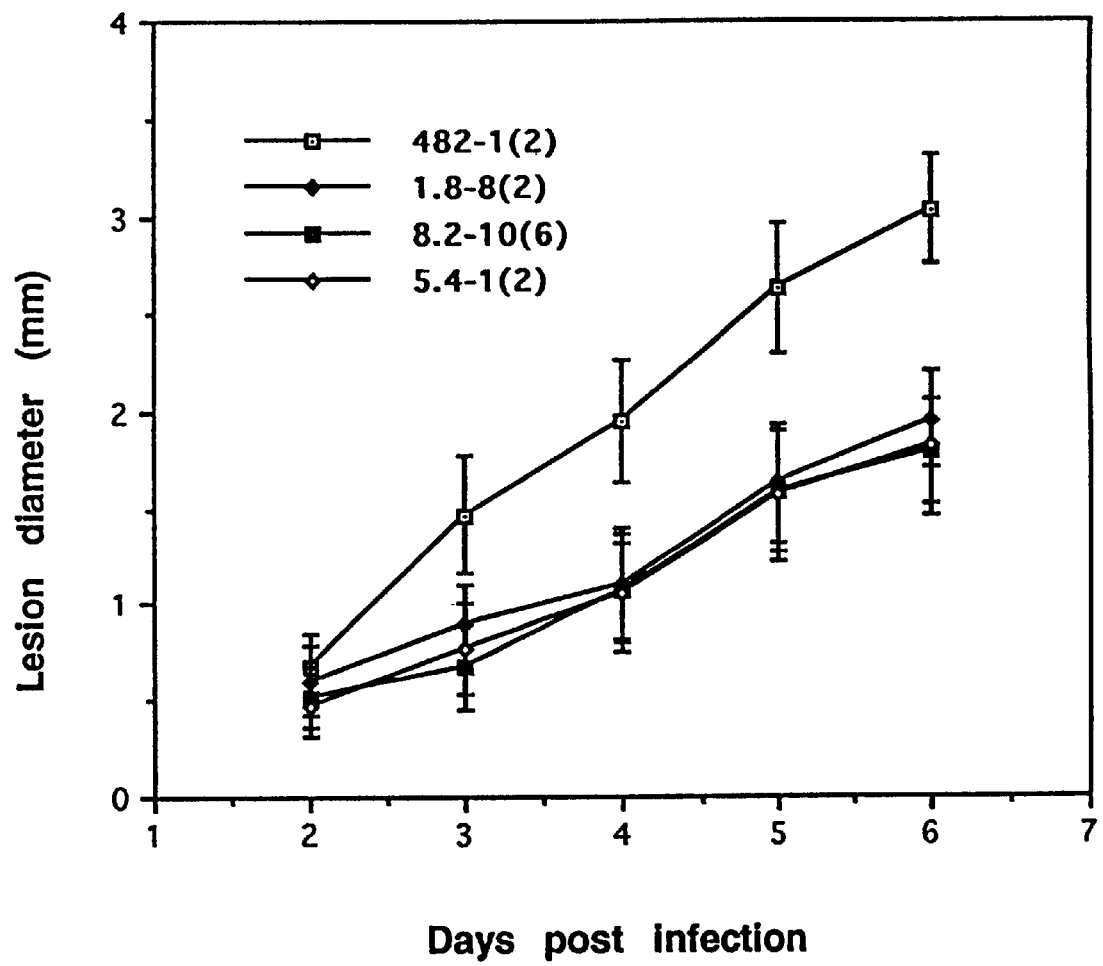
FIG. 9 is a graph illustrating the time course of lesion development in myb1 transgenic tobacco plants following infection with TMV. Each time point represents the mean diameter and standard deviation for 20 lesions measured. Numbers in parenthesis denote the individual T2 generation plants for the indicated lines. See footnote to Table 2 for a description of the plant lines.
Figure 10:
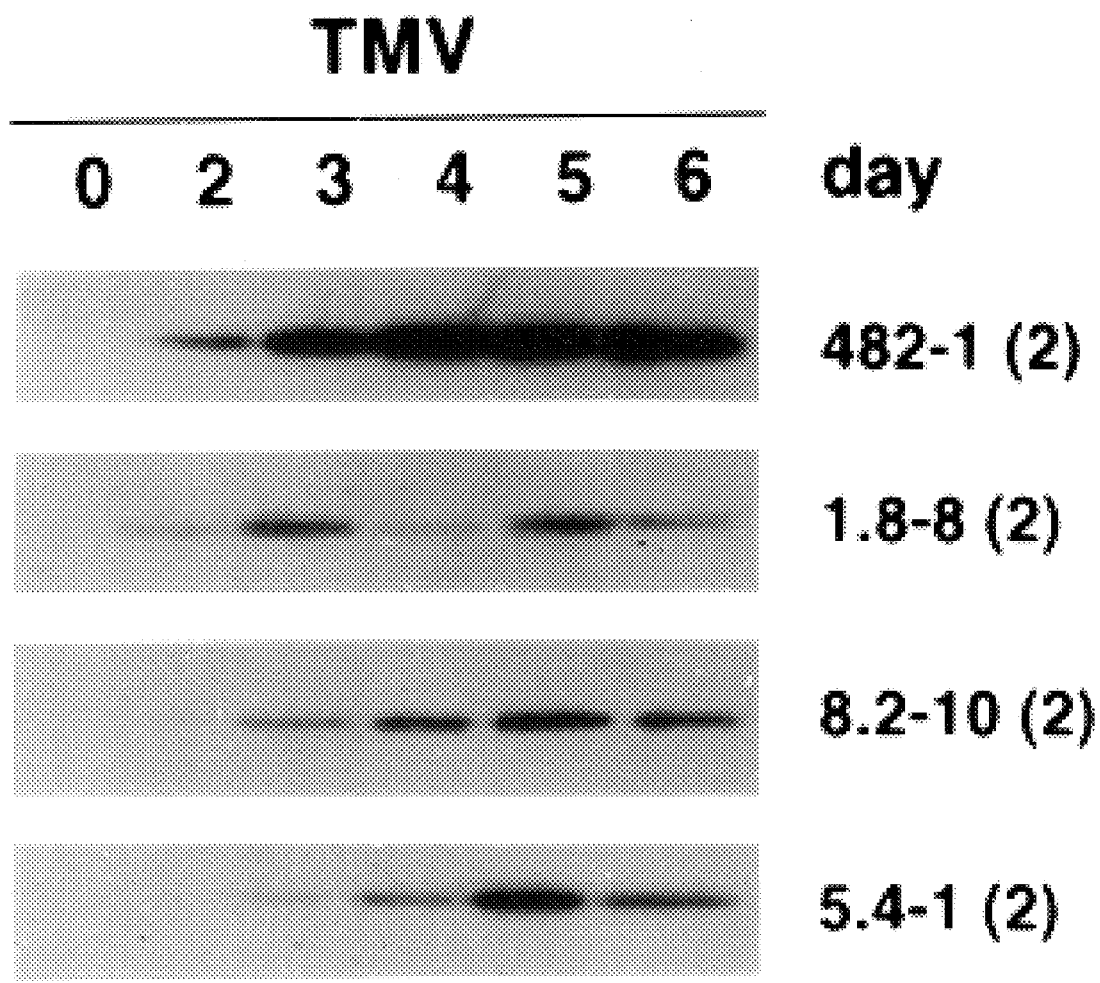
FIG. 10 is a western blot showing accumulation of TMV coat protein at lesion sites during the course of TMV infection. Three lesions (total about 1 cm$^2$) were punched out for each time point and pooled for protein extraction. Fifteen microliters of protein extract were fractionated on SDS-PAGE gel. TMV coat protein was detected using an anti-coat protein antibody. See footnote to Table 2 for a description of the plant lines.
Figure 11:
FIG. 11 is a photograph comparing TMV-infected leaves in a resistant myb1 transgenic plant and a vector-only transformed control plant. Shown here are transgenic lines 8.2-10 and 482-1. This photo was taken 8 days post inoculation with TMV.

Lesion development and TMV accumulation in infected leaves of representative T2 plants were closely monitored during the course of viral infection (FIG. 9). The transgenic plants with enhanced resistance exhibited significantly slower development of local lesion and eventually had much smaller lesions as compared to vector-only transformed control plants. Furthermore, these transgenic plants accumulated substantially lower levels of TMV at the lesion site, as indicated by the smaller amount of viral coat protein (FIG. 10). Presumably due to this greater restriction in lesion size and viral accumulation, heavily infected leaves of myb1 transgenic plants often remained viable for a much longer period of time than those of vector-only transformed control plants (FIG. 11). In sum, these transgenic plants exhibit inheritable increases in resistance which are manifested by the limitation of viral accumulation, reduction in lesion size and increased survival time of infected leaves.

Figure 12:
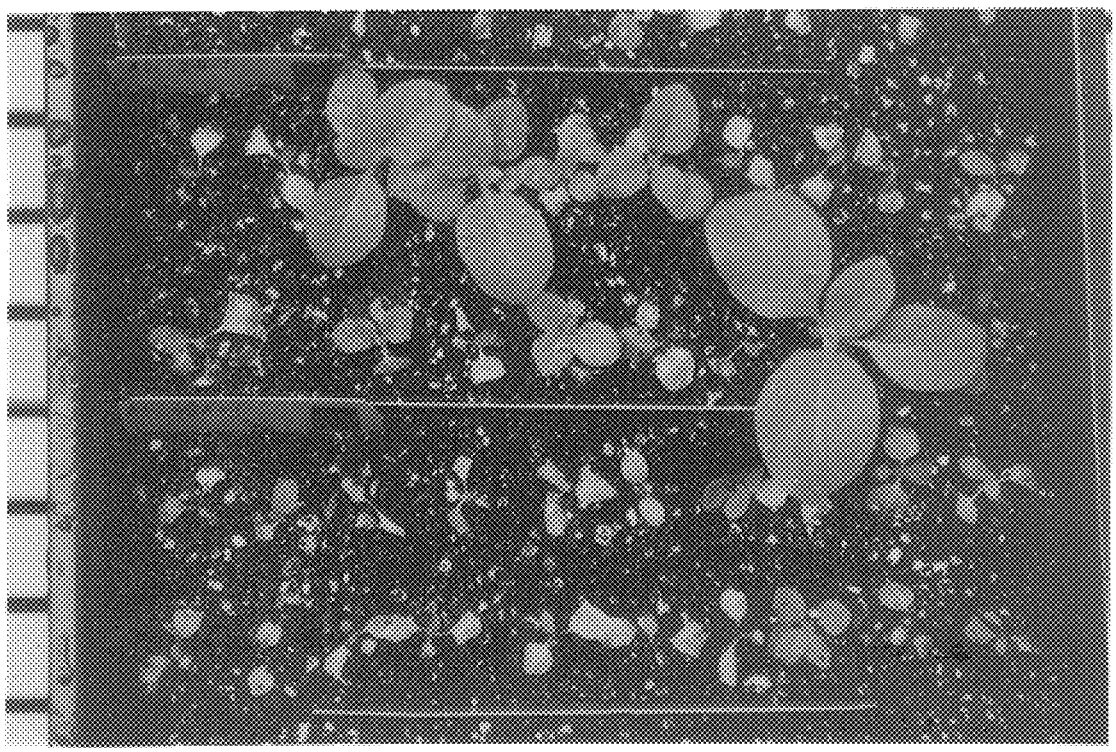
FIG. 12 is a photograph comparing control plants and myb1 transgenic plants (line 5.4-1) 14 days after growth in *Rhizoctonia solani*—infested soil.

Since tobacco Myb1 may regulate expression of PR proteins, many of which exhibit antifungal activity (8) and since other plant Myb proteins are involved in regulating biosynthesis of phenylpropanoids, which include many antifungal phytoalexins, several transgenic tobacco lines were tested for their resistance towards a virulent fungal pathogen, *Rhizoctonia solani*. This pathogen causes damping off disease in a wide variety of plant species. Preliminary data indicated that the myb1 transgenic tobacco lines with enhanced resistance to TMV also were less susceptible to *R. solani* (Table III, FIG. 12), suggesting that myb1 transgenic plants possess enhanced antiviral and antifungal properties.

TABLE III

Resistance of T2 Generation of myb1 Transgenic Plants to *R. solani*[a]

| Line[b] | Number of plants | | |
|---|---|---|---|
| | Resistant | Partially resistant | Susceptible |
| 482-1 | 0 | 0 | 20 |
| 8.2-10 | 1 | 1 | 18 |
| 5.4-1 | 3 | 3 | 14 |

[a]Twenty seedlings were tested for each lines. Disease symptoms were scored at 14 days post inoculation.
[b]See footnote to Table II for description of lines.

DISCUSSION

A major objective in studying plant disease resistance is to identify and characterize plant components crucial for signal transduction processes involved in activation of host defenses after pathogen attack. The present invention relates to a TMV-inducible myb oncogene homologue from tobacco with a demonstrable role in SA-mediated induction of plant defense responses. Activation of myb1 by TMV infections, which occurred during both the hypersensitive response and development of systemic acquired resistance, appears to depend on the N resistance gene-mediated signaling process and is closely associated with the rise of endogenous SA levels (1, FIG. 3 and 4). In addition to TMV, the incompatible bacterial pathogen *Pseudomonas syringae* pv. syringae also induced myb1 expression (FIG. 5). Exogenous treatment with SA rapidly activated expression of myb1, which preceded the induction of PR-1 genes (FIG. 6A). Furthermore, analysis of analogues of SA and INA showed a good correlation between biological activity of the analogues and their ability to induce myb1 gene expression (FIG. 6B). Together, these results suggest that myb1 encodes a signaling component downstream of SA. Although myb homologues have been isolated from several plant species, this is the first time that a myb gene has been shown to be involved in plant defense responses against microbial pathogens.

The transcription factor or factors that control PR gene expression have not yet been identified. Activation of the myb1 gene by SA did not require de novo protein synthesis and preceded induction of PR-1 genes which did require protein synthesis (FIG. 7). These results indicate that myb1 may encode a transcription factor involved in PR gene expression. The discovery of multiple MBS in the promoters of PR-1 and PR-2 genes and the specific binding of purified recombinant Myb1 protein to these sites in the PR-1a promoter (FIG. 8) further supports this model.

The tobacco Myb1 protein had different affinities for the two types of MBS (FIG. 8B) as reported for several other plant Myb proteins (11, 18). It preferentially bound to the MBSII (GTTTGGT) found in the PR-1a promoter (−520 to −514 bp). MBSII is a H-box-like sequence present in promoters of many genes involved in phenylpropanoid biosynthesis (e.g., pal, chs and dfr) and is implicated in the response to UV light and other environmental stresses (16). Indeed, the maize, petunia and Antirrhinum Myb transcription factors are known to control phenylpropanoid biosynthesis (11, 13, 16). Since many phytoalexins (compounds with antibacterial and antifungal activities) are derived from phenylpropanoids (27), tobacco Myb1 may not only regulate PR gene expression, but also transactivate phytoalexin biosynthetic genes that might be induced by TMV or SA.

There was a significant delay between SA activation of myb1 (within 15 minutes) and induction of PR-1 genes (between 6 to 12 hours; FIG. 6). This delay suggests that while myb1 activation by SA may be necessary, it is not sufficient for induction of PR-1 genes. Myb proteins are known to activate gene expression in combination with other transcription factors. The yeast Myb protein, BAS1, activates HIS4 transcription only in combination with the homeodomain protein, BAS2 (28). The chick c-Myb and v-Myb proteins require bZIP factors such as C/EBP to synergistically activate mim-1 gene expression (29), while maize Myb and Myc-like factors often act together to activate expression of flavonoid biosynthetic genes (11). Therefore, the tobacco Myb1 protein may need additional factor(s) such as bZIP- or Myc-related proteins for efficient activation of PR genes. In fact, the PR-1a promoter contains three Myc-binding consensus sequences (CANNTG) which are similar to the G-box core sequence (CACGTG) and may serve as binding sites for a Myc-related protein and/or a member of the bZIP class of G-box-binding proteins.

Rapid induction of myb1 gene expression by SA was insensitive to cycloheximide treatment (FIG. 7) and thus does not require de novo protein synthesis. In mammalian cells, members of the NF-kB family have been shown to transactivate the c-myb gene by binding to its first intron which contains NF-kB-binding sites (30). The transcription factor NF-kB is posttranscriptionally activated by reactive oxygen species such as $H_2O_2$ and mediates expression of many genes involved in acute phase, immune and inflammatory responses (31). In plants, elevation of $H_2O_2$ levels, due to inhibition of catalase and ascorbate peroxidase, appears to be one mode of SA action for induction of PR genes (6–8). By analogy, a posttranslationally activated NF-kB-like factor might be involved in the rapid activation of the tobacco myb1 gene by SA.

To further explore the potential role of myb1 in disease resistance and the transcriptional activation of PR-1, transgenic tobacco plants carrying myb1 sense or antisense constructs were generated and analyzed. Despite the lack of constitutive PR-1 gene expression in lines overexpressing myb1 gene in the sense orientation, a substantial number of transgenic plants carrying either sense or antisense myb1 constructs exhibited enhanced resistance to TMV, as indicated by a reduction in both viral accumulation and lesion size. In addition, the results presented herein indicate that transgenic plants with enhanced resistance to TMV are also less susceptible to a virulent fungal pathogen, *R. solani*.

The present results indicate that overexpression of the myb1 gene in its antisense orientation has the same effect as overexpression of myb1 in its sense orientation. While this seems perplexing at first, the data may be explained as follows. In antisense transgenic plants endogenous myb1 expression should be disrupted while in sense transgenic plants there should be high levels of myb1 gene product made from the chimeric transgene with its constitutive, powerful 35S promoter. However, in plants there is the phenomenon of co-suppression, in which introduction and presumed overexpression of the transgene actually results in suppression of transgene expression as well as expression of the corresponding endogenous gene copy (46). In other words, the expression of both transgene and its corresponding endogenous gene are co-suppressed. The molecular mechanism of co-suppression has not yet been fully elucidated. Depending on the plant species and transgene, co-suppression can occur in an significant portion of the transgenic plant population made with any given construct.

"Squelching" provides an alternative explanation for how presumed overexpression of a transgene gives the same result as that observed with an antisense construct (47, 48). During squelching, production of high levels of a transgene-encoded transcription factor, referred to herein as X for clarity, depresses the expression of gene(s) in which X normally does not play a regulatory role. Depression of expression levels of a gene(s) which X normally acts on to enhance the expression may also be observed. The likely molecular explanation for squelching is that high levels of factor X titrates out a second factor, hereinafter referred as Y, that is present in limited amounts and interacts with other factors (Z, W) besides X to facilitate transcription. If a complex composed of factors Y and Z or Y and W are required for expression of other gene(s), including the gene whose expression is normally enhanced by factor X, then excess X can remove or complex all the Y. This will prevent formation of YZ or YW complexes and thus block expression of genes requiring factor Y in complex with a third factor, for example Z or W.

Also perplexing is the observation that disruption of myb1 expression (through either antisense or co-suppression) or myb1 activity (through squelching) leads to enhanced resistance, since its expression in pathogen-infected or SA-treated tobacco correlated with resistance and PR-1 gene induction. This unexpected result may be explained as follows. Since plant myb genes are members of a large multigene family, overexpression of myb1 in the antisense orientation may also affect the expression of other tobacco myb genes. While sense-construct mediated co-suppression is likely to act on the corresponding endogenous gene only, overexpression of myb1 in the sense orientation might alter the transcriptional activity of other Myb factors. This again could be explained by squelching if one or more Myb members need to interact with a limiting factor that complexes with myb1 for transcriptional activity.

While many myb1 transgenic plants exhibited enhanced resistance to TMV, a few transgenic plants showed reduced resistance, as indicated by poor development of systemic acquired disease resistance and spread of virus from infected leaves to the stem or apex. This observation is preliminary and the data have not yet been repeated. However, the observed phenotype may be attributed to aberrant expression of myb1.

Altering myb1 expression levels, may lead to altered gene expression of other genes as well as changes in plant secondary metabolism, such as the biosynthesis of phenylpropanoids and other compounds, all of which could affect disease resistance. In fact, altered pigment deposition has been observed in the lesions induced by TMV infection of transgenic plants (purple lesions on myb1 transgenic plants vs. brown lesions on control plants, data not shown). This change in pigmentation likely results from altered biosynthesis of anthocyanins, which are derived from the phenylpropanoid pathway. Alternatively, myb1 might be suppressing expression of other, yet to be identified, genes which encode products with antiviral or antifungal activity. Blockage of myb1 expression or activity in the transgenic plants may lead to expression of the antiviral and antifungal genes and enhanced resistance to certain pathogens. Speculation on possible molecular mechanisms for the observed phenotype of the transgenic plants described herein are not intended to limit the scope of the invention in any way. Whatever the actual mechanism may be, the myb1 transgenic plants of the present invention exhibit enhanced disease resistance. Elucidation of the molecular mechanisms underlying the increased antiviral and antifungal properties of myb1 transgenic tobacco will further facilitate the development of transgenic plants with enhanced resistance to viral and fungal pathogens, the two most deleterious groups of disease-causing agents on crops.

REFERENCES

1. Malamy, J., Carr, J. P., Klessig, D. F. & Raskin, I. (1990) Science. 250, 1002–1004.
2. Métraux, J. P., Signer, H., Ryals, J., Ward, E., Wyss-Benz, M., Gaudin, J., Raschdorf, K., Schmid, E., Blum, W. & Inverardi, B. (1990) Science. 250, 1004–1006.
3. Gaffney, T., Friedrich, L., Vernooij, B., Negrotto, D., Nye, G., Uknes, S., Ward, E., Kessmann, H. & Ryals, J. (1993) Science 261, 754–756.
4. Delaney T., Uknes, S., Vernooij, B., Friedrich, L., Weymann, K., Negrotto, D., Gaffney, T., Gut-Rella, M., Kessmann, H., Ward, E. & Ryals, J. (1994) Science 266, 1247–1250.
5. Klessig, D. F. & Malamy J. (1994) Plant Mol. Biol. 26, 1439–1458.
6. Chen, Z., Silva, H. & Klessig, D. F. (1993) Science 262, 1883–1886.
7. Durner, J. & Klessig, D. F. (1995) Proc. Natl. Acad. Sci. USA 92, 11312–11316.
8. Dempsey, D. A. & Klessig, D. F. (1995) Bull. Inst. Pasteur 93, 167–186.
9. Graf, T. (1992) Cur. Opin. Genet. Dev. 2, 249–255
10. Thompson, M. A. & Ramsay, R. G. (1995) BioEssay 17, 341–350.
11. Grotewold, E., Drummond, B. J., Bowen, B. & Peterson, T. (1994) Cell 76, 543–53
12. Avila, J., Nieto, C., Canas, L., Benito, M. J. & Paz-Ares, J. (1993) Plant J. 3, 553–562.
13. Solano, R., Nieto, C. & Paz-Ares, J. (1995) EMBO J. 14, 1773
14. Baranowskij, N., Frohberg, C. & Willmitzer, L. (1994) EMBO J. 13, 5383
15. Jackson, D., Culianez-Macia, F. A., Prescott, A. G., Roberts, K. & Martin, C. (1991) Plant Cell 3, 115–125.
16. Sablowski, R. W., Moyano, E., Culianez-Macia, F. A., Schuch,W., Martin, C. & Bevan, M. A. (1994) EMBO J. 13, 128–137.
17. Oppenheimer, D. G., Herman, P. L., Sivakumaran, S., Esch, J. & Marks, M. D. (1991) Cell 67, 483–493.
18. Urao, T., Yamaguchi-Shinozaki, K., Urao, S. & Shinozaki, K. (1993) Plant Cell 5, 1529–1539.
19. Gubler, F., Kalla, R., Roberts, J. K. & Jacobsen, J. V. (1995) Plant Cell 7, 1879–1891.
20. Uknes, S., Dincher, S., Friedrich, L., Negrotto, D., Williams, S., Thompson-Tayler, H., Potter, S., Ward, E. & Ryals, J. (1993) Plant Cell 5, 159–169.
21. Church, G. M. & Gilbert, W. (1984) Proc. Natl.Acad. Sci. USA 81, 1991–1995.
22. Sambrook, J., Fritsch, E. F. & Maniatis, T. (1989) Molecular Cloning: A Laboratory Manual. 2nd Ed. Cold Spring Harbor Laboratory Press, Cold Spring Harbor, N.Y.
23. Malamy, J., Hennig, J. & Klessig, D. F. (1992) Plant Cell 4, 359–366.
24. Hennig, J., Malamy, J., Grynkiewicz, G., Indulski, J. and Klessig, D. F. (1993) Plant J. 4, 593–600.
25. Conrath, U., Chen, Z., Ricigliano, J. W. & Klessig, D. F. (1995) Proc. Natl. Acad. Sci. USA 92, 7143–7147.
26. Payne, G., Parks, T. D., Burkhart, W., Dincher, S., Ahl, P., Métraux, J. P., & Ryals, J. (1988) Plant Mol. Biol. 11, 89–94.

27. Dixon, R. A. & Paiva, N. L. (1995) Plant Cell 7, 1085–1097.
28. Tice-Baldwin, K., Fink, G. R. & Arndt, K. T. (1989) Science 246, 931–935.
29. Burk, O., Mink, S., Ringwald, M. & Klempnauer, K. H. (1993) EMBO J. 12, 2027–2038.
30. Toth, C. R., Hostutler, R. F., Baldwin, A. S., & Bender, T. P. (1995) J. Biol. Chem. 270, 7661–7671.
31. Shreck, R., Rieber, P. & Baeuerle, P. A. (1991) EMBO. J. 10, 2247–2258.
32. Whitham, S., Dinesh-Kumar, S. P., Choi, D., Hehl, R., Corr, C. & Baker, B. (1994) Cell 78, 1101–1115.
33. Fang, K. S. F., Vitale, M., Fehlner, P. & King, T. P. (1988) Proc. Natl. Acad. Sci. USA 85, 895–899.
34. Schuren, F. H. J., Asgeirsdóttir, S.A., Kothe, E. M., Scheer, J. M. J. & Wessels, J. G. H. (1993). J. Gen. Microbiol. 139, 2083–2090.
35. Murphy, E. V., Zhang, Y., Zhu, W. & Biggs, J. (1995) Gene 159, 131–135.
36. Alexander, D., Goodman, R. M., Gut-Rella, M., Glascook, C., Weymann, K., Friedrich, L., Maddox, D., Ahl-Goy, P., Luntz, T., Ward, E. & Ryals, J. (1993) Proc. Natl. Acad. Sci. USA 90, 7327–7331.
37. Niderman, T., Genetet, I., Bruyére, T., Gees, R., Stintzi, A., Legrand, M., Fritig, B. & Mösinger, E. (1995) Plant Physiol. 108, 17–27.
38. Mittler, R. & Lam, E. (1996) Trends in Microbiol. 4, 10–15.
39. An, G. (1986) Plant Physiol. 81: 86–91.
40. Dempsey, D. A. & Klessig, D. F. (1995) Bulletin de l'Institut Pasteur 93:167–186.
41. Gill, G. & Ptashne, M. (1988) Nature 334:721–724.
42. Goff, S. A., Cone, K. C. & Chandler, V. L. (1992) Genes Dev. 6:864–875
43. Horsch, R. B., Fry, J. E., Hoffman, N. L., Eicholtz, D., Rogers, S. D. & Fraley, R. T. (1985) Science 227:1229–1231.
44. Larkin, J. C., Oppenheimer, D. V., Lloyd, A. M. Paparozzi, E. T. & Marks, M. D. (1994) Plant Cell 6: 1065–1076.
45. Topfer, R., Matzeit, V., Gronenborn, B., Schell, J. & Steinbiss, H. (1987). Nucl. Acids Res. 15: 5890.
46. Baulcombe, D. C. & English, J. J. (1996) Curr. Opin. Biotechnol. 7:173–180.
47. R. Janknecht and T. Hunter, 1996 Nature 383:22 23.
48. C. Martin, 1996, Curr. Opin. Biotech 7:130–138)

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated nucleic acid molecule having a sequence that encodes SEQ ID NO:2.

2. A recombinant vector comprising the nucleic acid molecule of claim 1.

3. The recombinant DNA molecule of claim 2, wherein said vector is selected from the group consisting of Agrobacterium vectors, E. coli vectors, baculovirus vectors and S. cerevisiae vectors.

4. A method for enhancing a plants resistance to disease by delivering to said plant a vector as claimed in claim 3.

5. A method as claimed in claim 4 wherein said vector is delivered to said plant by a delivery means selected from the group consisting of Agrobacterium infection, polyethylene glycol fusion, electroporation, vacuum infiltration, and biolistic delivery of DNA coated metal particles.

6. A recombinant vector for the transformation of higher plants comprising a myb gene that encodes SEQ ID NO: 2, a strong constitutive promoter element, and a 3' regulatory segment to promote stability of mRNA, said myb gene being operably linked in a sense orientation to said promoter element such that expression of said myb gene is controlled by said promoter.

7. The recombinant vector of claim 6 wherein said strong constitutive promoter is selected from the group consisting of cauliflower mosaic virus 35S promoter and figwort mosaic virus 35S promoter.

8. A multicellular transgenic plant transformed with the recombinant vector of claim 6.

9. A recombinant vector for the transformation of higher plants comprising a myb gene that encodes SEQ ID NO:2, an inducible promoter element, and a 3' regulatory segment to promote stability of mRNA, said myb gene being operably linked in a sense orientation to said inducible promoter element such that expression of said myb gene is controlled by said promoter.

10. The recombinant vector of claim 9, wherein said inducible promoter is selected from the group consisting of the PR-1 promoter, the PR-2 promoter, and the tetracycline repressor/operator controlled promoter.

11. A multicellular transgenic plant transformed with the recombinant vector of claim 9.

12. A method for the production of a transgenic plant with enhanced disease resistance comprising:

a) providing a recombinant DNA construct in an Agrobacterium-based vector in which the coding region of a myb gene encoding SEQ ID NO:2 is operably linked in a sense orientation to a strong constitutive promoter, such that the expression of the myb gene is regulated by said promoter;

b) transforming a plant cell with said recombinant DNA construct; and c) regenerating a transgenic plant from said transformed cell.

13. The method of claim 12 wherein said strong constitutive promoter is selected from the group consisting of cauliflower mosaic virus 35S promoter and figwort mosaic virus 35S promoter.

14. A method for the production of a transgenic plant with enhanced disease resistance comprising:

a) providing a recombinant DNA construct in an Agrobacterium-based vector in which the coding region of a myb gene encoding SEQ ID NO:2 is operably linked in a sense orientation to an inducible promoter, such that the expression of the myb gene is regulated by said promoter;

b) transforming a plant cell with said recombinant DNA construct; and c) regenerating a transgenic plant from said transformed cell.

15. The method of claim 14, wherein said inducible promoter is selected from the group comprising the PR-1 promoter, the PR-2 promoter and the tetracycline repressor/operator controlled promoter.

16. The recombinant vector of claim 6, comprising SEQ ID NO:1.

17. The recombinant vector of claim 9, comprising SEQ ID NO:1.

18. The nucleic acid molecule of claim 1, having SEQ ID NO:1.

* * * * *